United States Patent
DeBelser et al.

(10) Patent No.: US 11,090,432 B2
(45) Date of Patent: Aug. 17, 2021

(54) ADVANCED STEP THERAPY DELIVERY FOR AN AMBULATORY INFUSION PUMP AND SYSTEM

(71) Applicant: Smiths Medical ASD, Inc., Plymouth, MN (US)

(72) Inventors: David DeBelser, Plymouth, MN (US); Clinton Robert Hetchler, Minnetonka, MN (US); David Pardee Sours, North Saint Paul, MN (US); Michael Wade Kersch, Saint Michael, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 187 days.

(21) Appl. No.: 16/023,505

(22) Filed: Jun. 29, 2018

(65) Prior Publication Data

US 2018/0304010 A1  Oct. 25, 2018

Related U.S. Application Data

(63) Continuation of application No. 14/525,579, filed on Oct. 28, 2014, now Pat. No. 10,016,559, which is a
(Continued)

(51) Int. Cl.
*A61M 5/172* (2006.01)
*A61M 5/142* (2006.01)
(Continued)

(52) U.S. Cl.
CPC ........ *A61M 5/172* (2013.01); *A61M 5/14244* (2013.01); *A61M 5/168* (2013.01);
(Continued)

(58) Field of Classification Search
CPC ................ A61M 2005/14208; A61M 5/14244
See application file for complete search history.

(56) References Cited

U.S. PATENT DOCUMENTS

| 2,462,596 A | 2/1949 | Bent et al. |
| 2,629,376 A | 2/1953 | Pierre et al. |

(Continued)

FOREIGN PATENT DOCUMENTS

| CN | 1618075 A | 5/2005 |
| CN | 1960775 A | 5/2007 |

(Continued)

OTHER PUBLICATIONS

Australian Patent Examination Report No. 1 dated Nov. 12, 2015 for Australian Patent Application No. 2010326338, 3 pages.
(Continued)

*Primary Examiner* — Laura A Bouchelle
(74) *Attorney, Agent, or Firm* — Patterson Thuente Pedersen, P.A.

(57) ABSTRACT

Embodiments relate to systems, methods and devices for delivering a drug or other therapy to a patient with an ambulatory infusion pump configured to provide a series of tolerance-building steps leading up to a plateau delivery rate. The plateau delivery rate is maintained until the prescribed amount of drug or therapy fluid is delivered to the patient. Embodiments of the invention include providing the patient or other user with a mechanism to decrease, or step down, the therapy delivery rate if a tolerance was not achieved at a lower rate, and providing notifications prior to a step up in a dosage delivery rate.

6 Claims, 10 Drawing Sheets

Related U.S. Application Data continuation of application No. 12/631,076, filed on Dec. 4, 2009, now Pat. No. 8,882,701.

(51) Int. Cl.
*A61M 5/168* (2006.01)
*G16H 40/63* (2018.01)
*G16H 20/17* (2018.01)

(52) U.S. Cl.
CPC ............ *G16H 20/17* (2018.01); *G16H 40/63* (2018.01); *A61M 2005/14208* (2013.01); *A61M 2205/3334* (2013.01); *A61M 2205/502* (2013.01)

(56) References Cited

U.S. PATENT DOCUMENTS

| | | | |
|---|---|---|---|
| 2,691,542 | A | 10/1954 | Chenoweth et al. |
| 3,059,639 | A | 10/1962 | Blackman et al. |
| 4,392,849 | A | 7/1983 | Petre et al. |
| 4,393,365 | A | 7/1983 | Kondo et al. |
| 4,475,901 | A | 10/1984 | Kraegen et al. |
| 5,000,664 | A | 3/1991 | Lawless et al. |
| 5,050,612 | A | 9/1991 | Matsumura |
| 5,122,362 | A | 6/1992 | Phillips et al. |
| 5,153,827 | A | 10/1992 | Coutre et al. |
| 5,181,910 | A | 1/1993 | Scanlon |
| 5,207,666 | A | 5/1993 | Idriss et al. |
| 5,219,330 | A | 6/1993 | Bollish et al. |
| 5,311,175 | A | 5/1994 | Waldman |
| 5,338,157 | A | 8/1994 | Blomquist |
| 5,362,562 | A | 11/1994 | Evans et al. |
| 5,364,346 | A | 11/1994 | Schrezenmeir |
| 5,368,562 | A | 11/1994 | Blomquist et al. |
| 5,376,070 | A | 12/1994 | Purvis et al. |
| 5,389,078 | A | 2/1995 | Zalesky et al. |
| 5,395,326 | A | 3/1995 | Haber et al. |
| 5,482,446 | A | 1/1996 | Williamson et al. |
| 5,485,408 | A | 1/1996 | Blomquist |
| 5,536,249 | A | 7/1996 | Castellano et al. |
| 5,551,850 | A | 9/1996 | Williamson et al. |
| 5,558,638 | A | 9/1996 | Evers et al. |
| 5,569,186 | A | 10/1996 | Lord et al. |
| 5,658,250 | A | 8/1997 | Blomquist et al. |
| 5,658,252 | A | 8/1997 | Johnson |
| 5,665,065 | A | 9/1997 | Colman et al. |
| 5,669,877 | A | 9/1997 | Blomquist |
| 5,674,240 | A | 10/1997 | Bonutti et al. |
| 5,681,285 | A | 10/1997 | Ford et al. |
| 5,685,844 | A | 11/1997 | Marttila |
| 5,695,473 | A | 12/1997 | Olsen |
| 5,713,856 | A | 2/1998 | Eggers et al. |
| 5,745,378 | A | 4/1998 | Barker et al. |
| 5,782,805 | A | 7/1998 | Meinzer et al. |
| 5,810,771 | A | 9/1998 | Blomquist |
| 5,814,015 | A | 9/1998 | Gargano et al. |
| 5,822,715 | A | 10/1998 | Worthington et al. |
| 5,876,370 | A | 3/1999 | Blomquist |
| 5,879,143 | A | 3/1999 | Cote et al. |
| 5,885,211 | A | 3/1999 | Eppstein et al. |
| 5,935,099 | A | 8/1999 | Peterson et al. |
| 5,935,106 | A | 8/1999 | Olsen |
| 5,960,403 | A | 9/1999 | Brown |
| 6,023,629 | A | 2/2000 | Tamada |
| 6,024,539 | A | 2/2000 | Blomquist |
| 6,077,055 | A | 6/2000 | Vilks |
| 6,122,536 | A | 9/2000 | Sun et al. |
| 6,142,939 | A | 11/2000 | Eppstein et al. |
| 6,175,752 | B1 | 1/2001 | Say et al. |
| 6,233,471 | B1 | 5/2001 | Berner et al. |
| 6,241,704 | B1 | 6/2001 | Peterson et al. |
| 6,248,057 | B1 | 6/2001 | Mavity et al. |
| 6,248,065 | B1 | 6/2001 | Brown |
| 6,248,067 | B1 | 6/2001 | Causey, III et al. |
| 6,249,717 | B1 | 6/2001 | Nicholson et al. |
| 6,255,781 | B1 | 7/2001 | Tsumura |
| 6,272,364 | B1 | 8/2001 | Kurnik |
| 6,298,254 | B2 | 10/2001 | Tamada |
| 6,306,420 | B1 | 10/2001 | Cheikh |
| 6,368,272 | B1 | 4/2002 | Porumbescu |
| 6,379,301 | B1 | 4/2002 | Worthington et al. |
| 6,422,057 | B1 | 7/2002 | Anderson |
| 6,475,180 | B2 | 11/2002 | Peterson et al. |
| 6,505,059 | B1 | 1/2003 | Kollias et al. |
| 6,517,482 | B1 | 2/2003 | Elden et al. |
| 6,535,714 | B2 | 3/2003 | Melker et al. |
| 6,539,250 | B1 | 3/2003 | Bettinger |
| 6,544,212 | B2 | 4/2003 | Galley et al. |
| 6,544,229 | B1 | 4/2003 | Danby et al. |
| 6,546,269 | B1 | 4/2003 | Kurnik |
| 6,551,276 | B1 | 4/2003 | Mann et al. |
| 6,553,244 | B2 | 4/2003 | Lesho et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,562,001 | B2 | 5/2003 | Lebel et al. |
| 6,565,509 | B1 | 5/2003 | Say et al. |
| 6,571,128 | B2 | 5/2003 | Lebel et al. |
| 6,577,899 | B2 | 6/2003 | Lebel et al. |
| 6,582,366 | B1 | 6/2003 | Porumbescu |
| 6,595,919 | B2 | 7/2003 | Berner et al. |
| 6,623,698 | B2 | 9/2003 | Kuo |
| 6,635,014 | B2 | 10/2003 | Starkweather et al. |
| 6,641,533 | B2 | 11/2003 | Causey, III et al. |
| 6,648,821 | B2 | 11/2003 | Lebel et al. |
| 6,650,951 | B1 | 11/2003 | Jones et al. |
| 6,656,114 | B1 | 12/2003 | Poulsen et al. |
| 6,659,978 | B1 | 12/2003 | Kasuga et al. |
| 6,668,196 | B1 | 12/2003 | Villegas et al. |
| 6,687,522 | B2 | 2/2004 | Tamada |
| 6,694,191 | B2 | 2/2004 | Starkweather et al. |
| 6,740,072 | B2 | 5/2004 | Starkweather et al. |
| 6,740,075 | B2 | 5/2004 | Lebel et al. |
| 6,744,350 | B2 | 6/2004 | Blomquist |
| 6,771,250 | B1 | 8/2004 | Oh |
| 6,773,412 | B2 | 8/2004 | O'Mahony et al. |
| 6,790,198 | B1 | 9/2004 | White et al. |
| 6,809,563 | B2 | 10/2004 | Schaal |
| 6,809,653 | B1 | 10/2004 | Mann et al. |
| 6,810,290 | B2 | 10/2004 | Lebel et al. |
| 6,827,702 | B2 | 12/2004 | Lebel et al. |
| 6,835,175 | B1 | 12/2004 | Porumbescu |
| 6,852,104 | B2 | 2/2005 | Blomquist |
| 6,862,466 | B2 | 3/2005 | Ackerman |
| 6,872,200 | B2 | 3/2005 | Mann et al. |
| 6,873,268 | B2 | 3/2005 | Lebel et al. |
| 6,880,564 | B2 | 4/2005 | Erickson |
| 6,882,940 | B2 | 4/2005 | Potts et al. |
| 6,895,263 | B2 | 5/2005 | Shin et al. |
| 6,902,905 | B2 | 6/2005 | Burson et al. |
| 6,918,542 | B2 | 7/2005 | Silverbrook et al. |
| 6,934,220 | B1 | 8/2005 | Cruitt et al. |
| 6,936,029 | B2 | 8/2005 | Mann et al. |
| 6,957,655 | B2 | 10/2005 | Erickson et al. |
| 6,958,705 | B2 | 10/2005 | Lebel et al. |
| 6,966,325 | B2 | 11/2005 | Erickson |
| 6,970,742 | B2 | 11/2005 | Mann et al. |
| 6,974,437 | B2 | 12/2005 | Lebel et al. |
| 6,979,326 | B2 | 12/2005 | Mann et al. |
| 6,997,920 | B2 | 2/2006 | Mann et al. |
| 6,998,387 | B1 | 2/2006 | Goke et al. |
| 6,999,854 | B2 | 2/2006 | Roth |
| 7,004,928 | B2 | 2/2006 | Aceti et al. |
| 7,022,072 | B2 | 4/2006 | Fox et al. |
| 7,025,743 | B2 | 4/2006 | Mann et al. |
| 7,033,338 | B2 | 4/2006 | Vilks et al. |
| 7,041,082 | B2 | 5/2006 | Blomquist et al. |
| 7,073,713 | B2 | 7/2006 | Silverbrook et al. |
| 7,083,108 | B2 | 8/2006 | Silverbrook et al. |
| 7,092,011 | B2 | 8/2006 | Silverbrook et al. |
| 7,097,104 | B2 | 8/2006 | Silverbrook et al. |
| 7,097,108 | B2 | 8/2006 | Zellner et al. |
| 7,098,803 | B2 | 8/2006 | Mann et al. |
| 7,109,878 | B2 | 9/2006 | Mann et al. |

(56) References Cited

U.S. PATENT DOCUMENTS

| | | |
|---|---|---|
| 7,150,741 B2 | 12/2006 | Erickson et al. |
| 7,156,808 B2 | 1/2007 | Quy |
| 7,179,226 B2 | 2/2007 | Crothall et al. |
| 7,181,505 B2 | 2/2007 | Haller et al. |
| 7,183,068 B2 | 2/2007 | Burson et al. |
| 7,187,404 B2 | 3/2007 | Silverbrook et al. |
| 7,201,319 B2 | 4/2007 | Silverbrook et al. |
| 7,204,823 B2 | 4/2007 | Estes et al. |
| 7,231,263 B2 | 6/2007 | Choi |
| 7,234,645 B2 | 6/2007 | Silverbrook et al. |
| 7,247,702 B2 | 7/2007 | Gardner et al. |
| 7,254,782 B1 | 8/2007 | Sherer |
| 7,267,665 B2 | 9/2007 | Steil et al. |
| 7,278,983 B2 | 10/2007 | Ireland et al. |
| 7,282,029 B1 | 10/2007 | Poulsen et al. |
| 7,289,142 B2 | 10/2007 | Silverbrook |
| 7,291,107 B2 | 11/2007 | Hellwig et al. |
| 7,295,867 B2 | 11/2007 | Berner et al. |
| 7,307,245 B2 | 12/2007 | Faries, Jr. et al. |
| 7,320,675 B2 | 1/2008 | Pastore et al. |
| 7,324,012 B2 | 1/2008 | Mann et al. |
| 7,341,577 B2 | 3/2008 | Gill |
| 7,347,836 B2 | 3/2008 | Peterson et al. |
| 7,362,971 B2 | 4/2008 | Silverbrook et al. |
| 7,373,083 B2 | 5/2008 | Silverbrook et al. |
| 7,377,706 B2 | 5/2008 | Silverbrook et al. |
| 7,399,277 B2 | 7/2008 | Saidara et al. |
| 7,404,796 B2 | 7/2008 | Ginsberg |
| 7,446,091 B2 | 11/2008 | Van Den Berghe |
| 7,460,152 B2 | 12/2008 | Silverbrook et al. |
| 7,464,010 B2 | 12/2008 | Yang et al. |
| 7,471,994 B2 | 12/2008 | Ford et al. |
| 7,475,825 B2 | 1/2009 | Silverbrook et al. |
| 7,483,050 B2 | 1/2009 | Silverbrook et al. |
| 7,483,743 B2 | 1/2009 | Mann et al. |
| 7,491,187 B2 | 2/2009 | Van Den Berghe et al. |
| 7,497,827 B2 | 3/2009 | Brister et al. |
| 7,515,060 B2 | 4/2009 | Blomquist |
| 7,524,045 B2 | 4/2009 | Silverbrook et al. |
| 7,534,226 B2 | 5/2009 | Mernoe et al. |
| 7,547,281 B2 | 6/2009 | Hayes et al. |
| 7,553,281 B2 | 6/2009 | Hellwig et al. |
| 7,556,613 B2 | 7/2009 | Wittmann et al. |
| 7,559,926 B1 | 7/2009 | Blischak |
| 7,569,030 B2 | 8/2009 | Lebel et al. |
| 7,588,046 B1 | 9/2009 | Erickson |
| 7,591,801 B2 | 9/2009 | Brauker et al. |
| 7,602,310 B2 | 10/2009 | Mann et al. |
| 7,604,593 B2 | 10/2009 | Parris et al. |
| 7,647,237 B2 | 1/2010 | Malave et al. |
| 7,651,489 B2 | 1/2010 | Estes et al. |
| 7,651,845 B2 | 1/2010 | Doyle, III et al. |
| 7,654,976 B2 | 2/2010 | Peterson et al. |
| 7,674,485 B2 | 3/2010 | Bhaskaran et al. |
| 7,676,519 B2 | 3/2010 | McBride et al. |
| 7,678,071 B2 | 3/2010 | Lebel et al. |
| 7,678,762 B2 | 3/2010 | Green et al. |
| 7,678,763 B2 | 3/2010 | Green et al. |
| 7,687,272 B1 | 3/2010 | Buchwald et al. |
| 7,697,967 B2 | 4/2010 | Stafford |
| 7,704,226 B2 | 4/2010 | Mueller, Jr. et al. |
| 7,708,717 B2 | 5/2010 | Estes et al. |
| 7,711,402 B2 | 5/2010 | Shults et al. |
| 7,715,893 B2 | 5/2010 | Kamath et al. |
| 7,717,903 B2 | 5/2010 | Estes et al. |
| 7,722,536 B2 | 5/2010 | Goodnow |
| 7,734,323 B2 | 6/2010 | Blomquist et al. |
| 7,751,907 B2 | 7/2010 | Blomquist |
| 7,766,829 B2 | 8/2010 | Sloan et al. |
| 7,766,830 B2 | 8/2010 | Fox et al. |
| 7,768,386 B2 | 8/2010 | Hayter et al. |
| 7,768,408 B2 | 8/2010 | Reggiardo et al. |
| 7,774,145 B2 | 8/2010 | Brauker et al. |
| 7,776,030 B2 | 8/2010 | Estes et al. |
| 7,778,680 B2 | 8/2010 | Goode, Jr. et al. |
| 7,785,313 B2 | 8/2010 | Mastrototaro |
| 7,794,426 B2 | 9/2010 | Briones et al. |
| 7,794,427 B2 | 9/2010 | Estes et al. |
| 7,794,428 B2 | 9/2010 | Estes et al. |
| 7,797,028 B2 | 9/2010 | Goode, Jr. et al. |
| 7,801,582 B2 | 9/2010 | Peyser |
| 7,806,853 B2 | 10/2010 | Wittmann et al. |
| 7,806,854 B2 | 10/2010 | Damiano et al. |
| 7,806,886 B2 | 10/2010 | Kanderian, Jr. et al. |
| 7,815,602 B2 | 10/2010 | Mann et al. |
| 7,819,843 B2 | 10/2010 | Mann et al. |
| 7,822,455 B2 | 10/2010 | Hoss et al. |
| 7,826,879 B2 | 11/2010 | Hoss et al. |
| 7,828,528 B2 | 11/2010 | Estes et al. |
| 7,831,310 B2 | 11/2010 | Lebel et al. |
| 7,833,196 B2 | 11/2010 | Estes et al. |
| 7,837,647 B2 | 11/2010 | Estes et al. |
| 7,837,651 B2 | 11/2010 | Bishop et al. |
| 7,850,641 B2 | 12/2010 | Lebel et al. |
| 7,860,544 B2 | 12/2010 | Say et al. |
| 7,869,851 B2 | 1/2011 | Hellwig et al. |
| 7,869,853 B1 | 1/2011 | Say et al. |
| 7,875,022 B2 | 1/2011 | Wenger et al. |
| 7,884,729 B2 | 2/2011 | Reggiardo et al. |
| 7,885,699 B2 | 2/2011 | Say et al. |
| 7,887,512 B2 | 2/2011 | Estes et al. |
| 7,890,295 B2 | 2/2011 | Shin et al. |
| 7,892,199 B2 | 2/2011 | Mhatre et al. |
| 7,901,394 B2 | 3/2011 | Ireland et al. |
| 7,912,674 B2 | 3/2011 | Killoren Clark et al. |
| 7,914,450 B2 | 3/2011 | Goode, Jr. et al. |
| 7,914,499 B2 | 3/2011 | Gonnelli et al. |
| 7,920,907 B2 | 4/2011 | McGarraugh et al. |
| 7,933,780 B2 | 4/2011 | De La Huerga |
| 7,935,076 B2 | 5/2011 | Estes et al. |
| 7,938,797 B2 | 5/2011 | Estes |
| 7,938,803 B2 | 5/2011 | Mernoe et al. |
| 7,941,200 B2 | 5/2011 | Weinert et al. |
| 7,946,985 B2 | 5/2011 | Mastrototaro et al. |
| 7,951,114 B2 | 5/2011 | Rush et al. |
| 7,959,598 B2 | 6/2011 | Estes |
| 7,963,946 B2 | 6/2011 | Moubayed et al. |
| 7,967,773 B2 | 6/2011 | Amborn et al. |
| 7,972,296 B2 | 7/2011 | Braig et al. |
| 7,976,492 B2 | 7/2011 | Brauker et al. |
| 7,981,034 B2 | 7/2011 | Jennewine et al. |
| 7,981,084 B2 | 7/2011 | Estes et al. |
| 7,981,102 B2 | 7/2011 | Patel et al. |
| 7,983,745 B2 | 7/2011 | Hatlestad et al. |
| 7,983,759 B2 | 7/2011 | Stahmann et al. |
| 7,985,330 B2 | 7/2011 | Wang et al. |
| 7,988,630 B1 | 8/2011 | Osorio et al. |
| 7,988,849 B2 | 8/2011 | Biewer et al. |
| 7,996,158 B2 | 8/2011 | Hayter et al. |
| 8,005,524 B2 | 8/2011 | Brauker et al. |
| 8,012,119 B2 | 9/2011 | Estes et al. |
| 8,016,783 B2 | 9/2011 | Pastore et al. |
| 8,025,634 B1 | 9/2011 | Moubayed et al. |
| 8,029,459 B2 | 10/2011 | Rush et al. |
| 8,029,460 B2 | 10/2011 | Rush et al. |
| 8,062,249 B2 | 11/2011 | Wilinska et al. |
| 8,066,665 B2 | 11/2011 | Rush et al. |
| 8,075,527 B2 | 12/2011 | Rush et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,093,212 B2 | 1/2012 | Gardner et al. |
| 8,105,268 B2 | 1/2012 | Lebel et al. |
| 8,105,279 B2 | 1/2012 | Mernoe et al. |
| 8,109,921 B2 | 2/2012 | Estes et al. |
| 8,114,350 B1 | 2/2012 | Silver et al. |
| 8,118,770 B2 | 2/2012 | Galley et al. |
| 8,119,593 B2 | 2/2012 | Richardson et al. |
| 8,127,046 B2 | 2/2012 | Grant et al. |
| 8,129,429 B2 | 3/2012 | Sporn et al. |
| 8,133,197 B2 | 3/2012 | Blomquist et al. |
| 8,140,275 B2 | 3/2012 | Campbell et al. |
| 8,140,312 B2 | 3/2012 | Hayter et al. |

(56) References Cited

U.S. PATENT DOCUMENTS

| | | |
|---|---|---|
| 8,147,446 B2 | 4/2012 | Yodfat et al. |
| 8,152,789 B2 | 4/2012 | Starkweather et al. |
| 8,170,721 B2 | 5/2012 | Nickerson |
| 8,177,716 B2 | 5/2012 | Say et al. |
| 8,182,445 B2 | 5/2012 | Moubayed et al. |
| 8,192,394 B2 | 6/2012 | Estes et al. |
| 8,192,395 B2 | 6/2012 | Estes et al. |
| 8,202,267 B2 | 6/2012 | Field et al. |
| 8,204,729 B2 | 6/2012 | Sher |
| 8,206,296 B2 | 6/2012 | Jennewine |
| 8,206,350 B2 | 6/2012 | Mann et al. |
| 8,208,984 B2 | 6/2012 | Blomquist et al. |
| 8,211,062 B2 | 7/2012 | Estes et al. |
| 8,219,222 B2 | 7/2012 | Blomquist |
| 8,221,345 B2 | 7/2012 | Blomquist |
| 8,221,385 B2 | 7/2012 | Estes |
| 8,226,558 B2 | 7/2012 | Say et al. |
| 8,226,891 B2 | 7/2012 | Sloan et al. |
| 8,231,562 B2 | 7/2012 | Buck et al. |
| 8,234,126 B1 | 7/2012 | Estes |
| 8,234,128 B2 | 7/2012 | Martucci et al. |
| 8,237,715 B2 | 8/2012 | Buck et al. |
| 8,246,540 B2 | 8/2012 | Ginsberg |
| 8,250,483 B2 | 8/2012 | Blomquist |
| 8,251,904 B2 | 8/2012 | Zivitz et al. |
| 8,251,906 B2 | 8/2012 | Brauker et al. |
| 8,257,259 B2 | 9/2012 | Brauker et al. |
| 8,257,300 B2 | 9/2012 | Budiman et al. |
| 8,260,630 B2 | 9/2012 | Brown |
| 8,262,617 B2 | 9/2012 | Aeschlimann et al. |
| 8,277,435 B2 | 10/2012 | Estes |
| 8,282,601 B2 | 10/2012 | Mernoe et al. |
| 8,287,454 B2 | 10/2012 | Wolpert et al. |
| 8,287,495 B2 | 10/2012 | Michaud et al. |
| 8,287,514 B2 | 10/2012 | Miller et al. |
| 8,290,562 B2 | 10/2012 | Goode, Jr. et al. |
| 8,298,184 B2 | 10/2012 | Diperna et al. |
| 8,311,749 B2 | 11/2012 | Brauker et al. |
| 8,323,188 B2 | 12/2012 | Tran |
| 8,328,754 B2 | 12/2012 | Estes et al. |
| 8,343,092 B2 | 1/2013 | Rush et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,348,886 B2 | 1/2013 | Kanderian, Jr. et al. |
| 8,348,923 B2 | 1/2013 | Kanderian, Jr. et al. |
| 8,349,319 B2 | 1/2013 | Schuchman et al. |
| 8,357,091 B2 | 1/2013 | Say et al. |
| 8,372,040 B2 | 2/2013 | Huang et al. |
| 8,376,943 B2 | 2/2013 | Kovach et al. |
| 8,377,031 B2 | 2/2013 | Hayter et al. |
| 8,380,273 B2 | 2/2013 | Say et al. |
| 8,409,131 B2 | 4/2013 | Say et al. |
| 8,414,523 B2 | 4/2013 | Blomquist et al. |
| 8,444,595 B2 | 5/2013 | Brukalo et al. |
| 8,449,523 B2 | 5/2013 | Brukalo et al. |
| 8,451,230 B2 | 5/2013 | Celentano et al. |
| 8,452,953 B2 | 5/2013 | Buck et al. |
| 8,454,510 B2 | 6/2013 | Yodfat et al. |
| 8,454,575 B2 | 6/2013 | Estes et al. |
| 8,454,576 B2 | 6/2013 | Mastrototaro et al. |
| 8,454,581 B2 | 6/2013 | Estes et al. |
| 8,460,231 B2 | 6/2013 | Brauker et al. |
| 8,465,460 B2 | 6/2013 | Yodfat et al. |
| 8,467,980 B2 | 6/2013 | Campbell et al. |
| 8,486,005 B2 | 7/2013 | Yodfat et al. |
| 8,552,880 B2 | 10/2013 | Kopp et al. |
| 8,562,558 B2 | 10/2013 | Kamath et al. |
| 8,573,027 B2 | 11/2013 | Rosinko et al. |
| 8,579,853 B2 | 11/2013 | Reggiardo et al. |
| 8,650,937 B2 | 2/2014 | Brown |
| 8,657,779 B2 | 2/2014 | Blomquist |
| 8,712,748 B2 | 4/2014 | Thukral et al. |
| 8,718,949 B2 | 5/2014 | Blomquist et al. |
| 8,726,266 B2 | 5/2014 | Kiaie et al. |
| 8,775,877 B2 | 7/2014 | Mcvey et al. |
| 8,801,657 B2 | 8/2014 | Blomquist et al. |
| 8,882,701 B2 | 11/2014 | Debelser et al. |
| 8,961,465 B2 | 2/2015 | Blomquist |
| 8,985,253 B2 | 3/2015 | Winter et al. |
| 8,986,253 B2 | 3/2015 | Diperna |
| 9,008,803 B2 | 4/2015 | Blomquist |
| 9,037,254 B2 | 5/2015 | John |
| 9,364,679 B2 | 6/2016 | John |
| 9,474,856 B2 | 10/2016 | Blomquist |
| 9,486,578 B2 | 11/2016 | Finan et al. |
| 9,833,177 B2 | 12/2017 | Blomquist |
| 10,016,559 B2 | 7/2018 | Debelser et al. |
| 10,052,049 B2 | 8/2018 | Blomquist et al. |
| 2001/0001144 A1 | 5/2001 | Kapp |
| 2001/0031944 A1 | 10/2001 | Peterson et al. |
| 2001/0037217 A1 | 11/2001 | Abensour et al. |
| 2001/0041831 A1 | 11/2001 | Starkweather et al. |
| 2002/0002326 A1 | 1/2002 | Causey et al. |
| 2002/0016568 A1 | 2/2002 | Lebel et al. |
| 2002/0065454 A1 | 5/2002 | Lebel et al. |
| 2002/0072932 A1 | 6/2002 | Swamy |
| 2002/0077852 A1 | 6/2002 | Ford et al. |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0032867 A1 | 2/2003 | Crothall et al. |
| 2003/0036683 A1 | 2/2003 | Kehr et al. |
| 2003/0050621 A1 | 3/2003 | Lebel et al. |
| 2003/0060765 A1 | 3/2003 | Campbell et al. |
| 2003/0065308 A1 | 4/2003 | Lebel et al. |
| 2003/0088238 A1 | 5/2003 | Poulsen et al. |
| 2003/0104982 A1 | 6/2003 | Wittmann et al. |
| 2003/0114836 A1 | 6/2003 | Estes et al. |
| 2003/0130616 A1 | 7/2003 | Steil et al. |
| 2003/0145854 A1 | 8/2003 | Hickle |
| 2003/0159945 A1 | 8/2003 | Miyazaki et al. |
| 2003/0160683 A1 | 8/2003 | Blomquist |
| 2003/0161744 A1 | 8/2003 | Vilks et al. |
| 2003/0163088 A1 | 8/2003 | Blomquist |
| 2003/0163090 A1 | 8/2003 | Blomquist et al. |
| 2003/0163223 A1 | 8/2003 | Blomquist |
| 2003/0163789 A1 | 8/2003 | Blomquist |
| 2003/0199854 A1 | 10/2003 | Kovach et al. |
| 2003/0208113 A1 | 11/2003 | Mault et al. |
| 2003/0212364 A1 | 11/2003 | Mann et al. |
| 2003/0212379 A1 | 11/2003 | Bylund et al. |
| 2003/0236489 A1 | 12/2003 | Jacobson et al. |
| 2004/0015102 A1 | 1/2004 | Cummings et al. |
| 2004/0015132 A1 | 1/2004 | Brown |
| 2004/0054263 A1 | 3/2004 | Moerman et al. |
| 2004/0068230 A1 | 4/2004 | Estes et al. |
| 2004/0073095 A1 | 4/2004 | Causey et al. |
| 2004/0115067 A1 | 6/2004 | Rush et al. |
| 2004/0152622 A1 | 8/2004 | Keith et al. |
| 2004/0167464 A1 | 8/2004 | Ireland et al. |
| 2004/0180810 A1 | 9/2004 | Pilarski |
| 2004/0193025 A1 | 9/2004 | Steil et al. |
| 2004/0193090 A1 | 9/2004 | Lebel et al. |
| 2004/0225252 A1 | 11/2004 | Gillespie et al. |
| 2004/0254434 A1 | 12/2004 | Goodnow et al. |
| 2005/0021006 A1 | 1/2005 | Tonnies |
| 2005/0022274 A1 | 1/2005 | Campbell et al. |
| 2005/0027182 A1 | 2/2005 | Siddiqui et al. |
| 2005/0030164 A1 | 2/2005 | Blomquist |
| 2005/0049179 A1 | 3/2005 | Davidson et al. |
| 2005/0050621 A1 | 3/2005 | Thomas |
| 2005/0065464 A1 | 3/2005 | Talbot et al. |
| 2005/0065760 A1 | 3/2005 | Murtfeldt et al. |
| 2005/0081847 A1 | 4/2005 | Lee et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0171513 A1 | 8/2005 | Mann et al. |
| 2005/0182358 A1 | 8/2005 | Veit et al. |
| 2005/0192557 A1 | 9/2005 | Brauker et al. |
| 2005/0197553 A1 | 9/2005 | Cooper |
| 2005/0197621 A1 | 9/2005 | Poulsen et al. |

(56) References Cited

U.S. PATENT DOCUMENTS

| | | |
|---|---|---|
| 2005/0203349 A1 | 9/2005 | Nanikashvili |
| 2005/0203360 A1 | 9/2005 | Brauker et al. |
| 2005/0228234 A1 | 10/2005 | Yang |
| 2005/0272640 A1 | 12/2005 | Doyle, III et al. |
| 2005/0277872 A1 | 12/2005 | Colby, Jr. et al. |
| 2005/0277912 A1 | 12/2005 | John |
| 2006/0001538 A1 | 1/2006 | Kraft et al. |
| 2006/0001550 A1 | 1/2006 | Mann et al. |
| 2006/0014670 A1 | 1/2006 | Green et al. |
| 2006/0031094 A1 | 2/2006 | Cohen et al. |
| 2006/0047192 A1 | 3/2006 | Hellwig et al. |
| 2006/0047538 A1 | 3/2006 | Condurso et al. |
| 2006/0060765 A1 | 3/2006 | Huang |
| 2006/0080059 A1 | 4/2006 | Stupp et al. |
| 2006/0085223 A1 | 4/2006 | Anderson et al. |
| 2006/0093785 A1 | 5/2006 | Hickle |
| 2006/0094985 A1 | 5/2006 | Aceti et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0167345 A1 | 7/2006 | Vespasiani |
| 2006/0173406 A1 | 8/2006 | Hayes et al. |
| 2006/0173444 A1 | 8/2006 | Choy et al. |
| 2006/0202859 A1 | 9/2006 | Mastrototaro et al. |
| 2006/0224109 A1 | 10/2006 | Steil et al. |
| 2006/0253097 A1 | 11/2006 | Braig et al. |
| 2006/0253296 A1 | 11/2006 | Liisberg et al. |
| 2006/0264895 A1 | 11/2006 | Flanders |
| 2006/0271020 A1 | 11/2006 | Huang et al. |
| 2006/0272652 A1 | 12/2006 | Stocker et al. |
| 2006/0276771 A1 | 12/2006 | Galley et al. |
| 2007/0016127 A1 | 1/2007 | Staib et al. |
| 2007/0016170 A1 | 1/2007 | Kovelman |
| 2007/0016449 A1 | 1/2007 | Cohen et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc et al. |
| 2007/0060874 A1 | 3/2007 | Nesbitt et al. |
| 2007/0066956 A1 | 3/2007 | Finkel |
| 2007/0073236 A1 | 3/2007 | Mernoe et al. |
| 2007/0083152 A1* | 4/2007 | Williams, Jr. ......... G16H 20/17 604/65 |
| 2007/0083335 A1 | 4/2007 | Moerman |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0112298 A1 | 5/2007 | Mueller, Jr. et al. |
| 2007/0112299 A1 | 5/2007 | Smit et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0156033 A1 | 7/2007 | Causey, III et al. |
| 2007/0156092 A1 | 7/2007 | Estes et al. |
| 2007/0156457 A1 | 7/2007 | Brown |
| 2007/0167905 A1 | 7/2007 | Estes et al. |
| 2007/0167912 A1 | 7/2007 | Causey et al. |
| 2007/0173712 A1 | 7/2007 | Shah et al. |
| 2007/0173762 A1 | 7/2007 | Estes et al. |
| 2007/0179355 A1 | 8/2007 | Rosen |
| 2007/0179444 A1 | 8/2007 | Causey et al. |
| 2007/0203454 A1 | 8/2007 | Shermer et al. |
| 2007/0213657 A1 | 9/2007 | Jennewine et al. |
| 2007/0233051 A1 | 10/2007 | Hohl et al. |
| 2007/0245258 A1 | 10/2007 | Ginggen et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0287985 A1 | 12/2007 | Estes et al. |
| 2007/0299389 A1 | 12/2007 | Halbert et al. |
| 2008/0004601 A1 | 1/2008 | Jennewine et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0058773 A1 | 3/2008 | John |
| 2008/0065007 A1 | 3/2008 | Peterson et al. |
| 2008/0065016 A1 | 3/2008 | Peterson et al. |
| 2008/0071209 A1 | 3/2008 | Moubayed et al. |
| 2008/0071210 A1 | 3/2008 | Moubayed et al. |
| 2008/0071217 A1 | 3/2008 | Moubayed et al. |
| 2008/0071251 A1* | 3/2008 | Moubayed ............ A61M 5/172 604/890.1 |
| 2008/0071580 A1 | 3/2008 | Marcus et al. |
| 2008/0076969 A1 | 3/2008 | Kraft et al. |
| 2008/0097289 A1 | 4/2008 | Steil et al. |
| 2008/0106431 A1 | 5/2008 | Blomquist |
| 2008/0114299 A1 | 5/2008 | Damgaard-Sorensen et al. |
| 2008/0132844 A1 | 6/2008 | Peterson et al. |
| 2008/0139907 A1 | 6/2008 | Rao et al. |
| 2008/0147004 A1 | 6/2008 | Mann et al. |
| 2008/0147041 A1 | 6/2008 | Kristensen |
| 2008/0147042 A1 | 6/2008 | Pettis et al. |
| 2008/0147050 A1 | 6/2008 | Mann et al. |
| 2008/0154513 A1 | 6/2008 | Kovatchev et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist et al. |
| 2008/0183060 A1 | 7/2008 | Steil et al. |
| 2008/0206799 A1 | 8/2008 | Blomquist |
| 2008/0228056 A1 | 9/2008 | Blomquist et al. |
| 2008/0249470 A1 | 10/2008 | Malave et al. |
| 2008/0255438 A1 | 10/2008 | Saidara et al. |
| 2008/0255517 A1 | 10/2008 | Nair et al. |
| 2008/0264024 A1 | 10/2008 | Baaken |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0294294 A1 | 11/2008 | Blomquist |
| 2008/0300534 A1 | 12/2008 | Blomquist |
| 2008/0300572 A1 | 12/2008 | Rankers et al. |
| 2008/0300651 A1 | 12/2008 | Gerber et al. |
| 2008/0306434 A1 | 12/2008 | Dobbles et al. |
| 2008/0306444 A1 | 12/2008 | Brister et al. |
| 2008/0312585 A1 | 12/2008 | Brukalo et al. |
| 2009/0005726 A1 | 1/2009 | Jones et al. |
| 2009/0018779 A1 | 1/2009 | Cohen et al. |
| 2009/0030733 A1 | 1/2009 | Cohen et al. |
| 2009/0036753 A1 | 2/2009 | King |
| 2009/0054475 A1 | 2/2009 | Chen et al. |
| 2009/0067989 A1 | 3/2009 | Estes et al. |
| 2009/0069745 A1 | 3/2009 | Estes et al. |
| 2009/0069749 A1 | 3/2009 | Miller et al. |
| 2009/0069787 A1 | 3/2009 | Estes et al. |
| 2009/0085768 A1 | 4/2009 | Patel et al. |
| 2009/0088731 A1 | 4/2009 | Campbell et al. |
| 2009/0093756 A1 | 4/2009 | Minaie et al. |

(56) References Cited

U.S. PATENT DOCUMENTS

| | | |
|---|---|---|
| 2009/0105636 A1 | 4/2009 | Hayter et al. |
| 2009/0105646 A1 | 4/2009 | Hendrixson et al. |
| 2009/0112626 A1 | 4/2009 | Talbot et al. |
| 2009/0118592 A1 | 5/2009 | Klitgaard |
| 2009/0131860 A1 | 5/2009 | Nielsen |
| 2009/0131861 A1 | 5/2009 | Braig et al. |
| 2009/0143661 A1 | 6/2009 | Taub et al. |
| 2009/0150186 A1 | 6/2009 | Cohen et al. |
| 2009/0150865 A1 | 6/2009 | Young et al. |
| 2009/0156990 A1 | 6/2009 | Wenger et al. |
| 2009/0157003 A1 | 6/2009 | Jones et al. |
| 2009/0163855 A1 | 6/2009 | Shin et al. |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba, Jr. et al. |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0212966 A1 | 8/2009 | Panduro |
| 2009/0216100 A1 | 8/2009 | Ebner et al. |
| 2009/0240193 A1 | 9/2009 | Mensinger et al. |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0270810 A1 | 10/2009 | Debelser et al. |
| 2009/0275886 A1 | 11/2009 | Blomquist et al. |
| 2009/0275887 A1 | 11/2009 | Estes |
| 2009/0281393 A1 | 11/2009 | Smith |
| 2010/0008795 A1 | 1/2010 | Diperna |
| 2010/0010330 A1 | 1/2010 | Rankers et al. |
| 2010/0030045 A1 | 2/2010 | Gottlieb et al. |
| 2010/0030387 A1 | 2/2010 | Sen |
| 2010/0049164 A1 | 2/2010 | Estes |
| 2010/0056993 A1 | 3/2010 | Chase |
| 2010/0057043 A1 | 3/2010 | Kovatchev et al. |
| 2010/0064257 A1 | 3/2010 | Buck et al. |
| 2010/0069730 A1 | 3/2010 | Bergstrom et al. |
| 2010/0081993 A1 | 4/2010 | O'Connor |
| 2010/0094110 A1 | 4/2010 | Heller et al. |
| 2010/0094251 A1 | 4/2010 | Estes |
| 2010/0095229 A1 | 4/2010 | Dixon et al. |
| 2010/0105999 A1 | 4/2010 | Dixon et al. |
| 2010/0114015 A1 | 5/2010 | Kanderian, Jr. et al. |
| 2010/0121169 A1 | 5/2010 | Petisce et al. |
| 2010/0121170 A1 | 5/2010 | Rule |
| 2010/0125241 A1 | 5/2010 | Prud Homme et al. |
| 2010/0130933 A1 | 5/2010 | Holland et al. |
| 2010/0138197 A1 | 6/2010 | Sher |
| 2010/0145276 A1 | 6/2010 | Yodfat et al. |
| 2010/0156633 A1 | 6/2010 | Buck, Jr. et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0174266 A1 | 7/2010 | Estes |
| 2010/0174553 A1 | 7/2010 | Kaufman et al. |
| 2010/0179402 A1 | 7/2010 | Goode, Jr. et al. |
| 2010/0185142 A1 | 7/2010 | Kamen et al. |
| 2010/0185152 A1 | 7/2010 | Larsen et al. |
| 2010/0185175 A1 | 7/2010 | Kamen et al. |
| 2010/0192686 A1 | 8/2010 | Kamen et al. |
| 2010/0198034 A1 | 8/2010 | Thomas et al. |
| 2010/0198142 A1 | 8/2010 | Sloan et al. |
| 2010/0202040 A1 | 8/2010 | Morgan |
| 2010/0205001 A1 | 8/2010 | Knudsen et al. |
| 2010/0218132 A1 | 8/2010 | Soni et al. |
| 2010/0222765 A1 | 9/2010 | Blomquist et al. |
| 2010/0228186 A1 | 9/2010 | Estes et al. |
| 2010/0234709 A1 | 9/2010 | Say et al. |
| 2010/0235439 A1 | 9/2010 | Goodnow |
| 2010/0249530 A1 | 9/2010 | Rankers et al. |
| 2010/0249561 A1 | 9/2010 | Patek et al. |
| 2010/0261987 A1 | 10/2010 | Kamath et al. |
| 2010/0262078 A1 | 10/2010 | Blomquist |
| 2010/0262117 A1 | 10/2010 | Magni et al. |
| 2010/0262434 A1 | 10/2010 | Shaya |
| 2010/0274592 A1 | 10/2010 | Nitzan et al. |
| 2010/0274751 A1 | 10/2010 | Blomquist |
| 2010/0277119 A1 | 11/2010 | Montague et al. |
| 2010/0280329 A1 | 11/2010 | Randloev et al. |
| 2010/0286563 A1 | 11/2010 | Bryer et al. |
| 2010/0286601 A1 | 11/2010 | Yodfat et al. |
| 2010/0286653 A1 | 11/2010 | Kubel et al. |
| 2010/0292634 A1 | 11/2010 | Kircher, Jr. et al. |
| 2010/0295686 A1 | 11/2010 | Sloan et al. |
| 2010/0298681 A1 | 11/2010 | Say et al. |
| 2010/0298685 A1 | 11/2010 | Hayter et al. |
| 2010/0305545 A1 | 12/2010 | Kanderian, Jr. et al. |
| 2010/0305965 A1 | 12/2010 | Benjamin et al. |
| 2010/0312085 A1 | 12/2010 | Andrews et al. |
| 2010/0317950 A1 | 12/2010 | Galley et al. |
| 2010/0324382 A1 | 12/2010 | Cantwell et al. |
| 2010/0324398 A1 | 12/2010 | Tzyy-Ping |
| 2010/0331651 A1 | 12/2010 | Groll |
| 2011/0004188 A1 | 1/2011 | Shekalim |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0015509 A1 | 1/2011 | Peyser |
| 2011/0021898 A1 | 1/2011 | Wei et al. |
| 2011/0022025 A1 | 1/2011 | Savoie et al. |
| 2011/0033833 A1 | 2/2011 | Blomquist et al. |
| 2011/0040247 A1 | 2/2011 | Mandro et al. |
| 2011/0040251 A1 | 2/2011 | Blomquist et al. |
| 2011/0047499 A1 | 2/2011 | Mandro et al. |
| 2011/0050428 A1 | 3/2011 | Istoc |
| 2011/0053121 A1 | 3/2011 | Heaton |
| 2011/0054390 A1 | 3/2011 | Searle et al. |
| 2011/0054391 A1 | 3/2011 | Ward et al. |
| 2011/0056264 A1 | 3/2011 | Kaplan et al. |
| 2011/0058485 A1 | 3/2011 | Sloan |
| 2011/0060281 A1 | 3/2011 | Aeschlimann et al. |
| 2011/0071372 A1 | 3/2011 | Sloan et al. |
| 2011/0071464 A1 | 3/2011 | Palerm |
| 2011/0071465 A1 | 3/2011 | Wang et al. |
| 2011/0071765 A1 | 3/2011 | Yodfat et al. |
| 2011/0077481 A1 | 3/2011 | Say et al. |
| 2011/0077963 A1 | 3/2011 | Knudsen et al. |
| 2011/0082439 A1 | 4/2011 | Wenger et al. |
| 2011/0087165 A1 | 4/2011 | Amborn et al. |
| 2011/0092788 A1 | 4/2011 | Long et al. |
| 2011/0092894 A1 | 4/2011 | McGill et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0105955 A1 | 5/2011 | Yudovsky et al. |
| 2011/0106011 A1 | 5/2011 | Cinar et al. |
| 2011/0106049 A1 | 5/2011 | Damiano et al. |
| 2011/0106050 A1 | 5/2011 | Yodfat et al. |
| 2011/0112504 A1 | 5/2011 | Causey et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118662 A1 | 5/2011 | Mhatre et al. |
| 2011/0118699 A1 | 5/2011 | Yodfat et al. |
| 2011/0124996 A1 | 5/2011 | Reinke et al. |
| 2011/0124999 A1 | 5/2011 | Reggiardo et al. |
| 2011/0125085 A1 | 5/2011 | McGill et al. |
| 2011/0126188 A1 | 5/2011 | Bernstein et al. |
| 2011/0130716 A1 | 6/2011 | Estes et al. |
| 2011/0130746 A1 | 6/2011 | Budiman |
| 2011/0133946 A1 | 6/2011 | Kopp et al. |
| 2011/0137239 A1 | 6/2011 | Debelser et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0160654 A1 | 6/2011 | Hanson et al. |

(56) References Cited

U.S. PATENT DOCUMENTS

| | | |
|---|---|---|
| 2011/0160695 A1 | 6/2011 | Sigrist et al. |
| 2011/0166544 A1 | 7/2011 | Verhoef et al. |
| 2011/0166875 A1 | 7/2011 | Hayter et al. |
| 2011/0172744 A1 | 7/2011 | Davis et al. |
| 2011/0178461 A1 | 7/2011 | Chong et al. |
| 2011/0178462 A1 | 7/2011 | Moberg et al. |
| 2011/0178717 A1 | 7/2011 | Goodnow et al. |
| 2011/0184264 A1 | 7/2011 | Galasso et al. |
| 2011/0184342 A1 | 7/2011 | Pesach et al. |
| 2011/0190701 A1 | 8/2011 | Remde et al. |
| 2011/0196213 A1 | 8/2011 | Thukral et al. |
| 2011/0202040 A1 | 8/2011 | Remde et al. |
| 2011/0205065 A1 | 8/2011 | Strachan et al. |
| 2011/0208155 A1 | 8/2011 | Palerm et al. |
| 2011/0213225 A1 | 9/2011 | Bernstein et al. |
| 2011/0213306 A1 | 9/2011 | Hanson et al. |
| 2011/0256024 A1 | 10/2011 | Cole et al. |
| 2011/0257625 A1 | 10/2011 | Jasperson et al. |
| 2011/0257895 A1 | 10/2011 | Brauker et al. |
| 2011/0266999 A1 | 11/2011 | Yodfat et al. |
| 2012/0013625 A1 | 1/2012 | Blomquist et al. |
| 2012/0013802 A1 | 1/2012 | Blomquist et al. |
| 2012/0029433 A1 | 2/2012 | Michaud et al. |
| 2012/0029941 A1 | 2/2012 | Malave et al. |
| 2012/0030610 A1 | 2/2012 | Diperna et al. |
| 2012/0041415 A1 | 2/2012 | Estes et al. |
| 2012/0053522 A1 | 3/2012 | Yodfat et al. |
| 2012/0059353 A1 | 3/2012 | Kovatchev et al. |
| 2012/0059673 A1 | 3/2012 | Cohen et al. |
| 2012/0095315 A1 | 4/2012 | Tenbarge et al. |
| 2012/0109100 A1 | 5/2012 | Estes et al. |
| 2012/0123230 A1 | 5/2012 | Brown et al. |
| 2012/0163481 A1 | 6/2012 | Ebner et al. |
| 2012/0185267 A1 | 7/2012 | Kamen et al. |
| 2012/0191061 A1 | 7/2012 | Yodfat et al. |
| 2012/0191063 A1 | 7/2012 | Brauker et al. |
| 2012/0226124 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0265722 A1 | 10/2012 | Blomquist |
| 2012/0296269 A1 | 11/2012 | Blomquist |
| 2012/0330227 A1 | 12/2012 | Budiman et al. |
| 2013/0012917 A1 | 1/2013 | Miller et al. |
| 2013/0053816 A1 | 2/2013 | Diperna et al. |
| 2013/0131630 A1 | 5/2013 | Blomquist |
| 2013/0324928 A1 | 12/2013 | Kruse |
| 2013/0331790 A1 | 12/2013 | Brown et al. |
| 2013/0345625 A1 | 12/2013 | Causey, III et al. |
| 2013/0345663 A1 | 12/2013 | Agrawal et al. |
| 2014/0012511 A1 | 1/2014 | Mensinger et al. |
| 2014/0019396 A1 | 1/2014 | Carlsgaard et al. |
| 2014/0066890 A1 | 3/2014 | Sloan et al. |
| 2014/0074059 A1 | 3/2014 | Howell et al. |
| 2014/0137641 A1 | 5/2014 | Brown |
| 2014/0171772 A1 | 6/2014 | Blomquist |
| 2014/0273042 A1 | 9/2014 | Saint |
| 2014/0275419 A1 | 9/2014 | Ward et al. |
| 2014/0276419 A1 | 9/2014 | Rosinko et al. |
| 2014/0276420 A1 | 9/2014 | Rosinko |
| 2014/0276531 A1 | 9/2014 | Walsh |
| 2014/0276553 A1 | 9/2014 | Rosinko et al. |
| 2014/0276556 A1 | 9/2014 | Saint et al. |
| 2014/0276570 A1 | 9/2014 | Saint |
| 2014/0276574 A1 | 9/2014 | Saint |
| 2014/0350371 A1 | 11/2014 | Blomquist et al. |
| 2014/0378898 A1 | 12/2014 | Rosinko |
| 2015/0045770 A1 | 2/2015 | Debelser et al. |
| 2015/0073337 A1 | 3/2015 | Saint et al. |
| 2015/0182693 A1 | 7/2015 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0030669 A1 | 2/2016 | Harris et al. |
| 2016/0082188 A1 | 3/2016 | Blomquist et al. |
| 2016/0199571 A1 | 7/2016 | Rosinko et al. |
| 2016/0228041 A1 | 8/2016 | Heller et al. |
| 2017/0000943 A1 | 1/2017 | Blomquist et al. |
| 2018/0092578 A1 | 4/2018 | Blomquist |

FOREIGN PATENT DOCUMENTS

| | | |
|---|---|---|
| CN | 101254325 A | 9/2008 |
| CN | 101579545 A | 11/2009 |
| DE | 399065 | 7/1924 |
| DE | 4407005 C1 | 3/1995 |
| DE | 19819407 A1 | 11/1999 |
| DE | 10121317 A1 | 11/2002 |
| DE | 10352456 A1 | 7/2005 |
| EP | 1102194 A2 | 5/2001 |
| EP | 1571582 A2 | 9/2005 |
| EP | 1500029 B1 | 4/2007 |
| JP | 2006034323 A | 2/2006 |
| JP | 2010503515 A | 2/2010 |
| WO | WO-0045696 A1 | 8/2000 |
| WO | WO-0074753 A1 | 12/2000 |
| WO | WO-0152727 A1 | 7/2001 |
| WO | WO-02062212 A2 | 8/2002 |
| WO | WO-03082091 A2 | 10/2003 |
| WO | WO-2005046559 A2 | 5/2005 |
| WO | WO-2006061169 A1 | 6/2006 |
| WO | WO-2006127841 A2 | 11/2006 |
| WO | WO-2007000425 A2 | 1/2007 |
| WO | WO-2007056592 A2 | 5/2007 |
| WO | WO-2007089537 A1 | 8/2007 |
| WO | WO-2007149533 A2 | 12/2007 |
| WO | WO-2008036658 A2 | 3/2008 |
| WO | WO-2008048556 A2 | 4/2008 |
| WO | WO-2008048582 A1 | 4/2008 |
| WO | WO-2008048583 A1 | 4/2008 |
| WO | WO-2008048584 A1 | 4/2008 |
| WO | WO-2008048585 A1 | 4/2008 |
| WO | WO-2008048586 A1 | 4/2008 |
| WO | WO-2008048587 A1 | 4/2008 |
| WO | WO-2008064254 A2 | 5/2008 |
| WO | WO-2008091320 A2 | 7/2008 |
| WO | WO-2008103175 A1 | 8/2008 |
| WO | WO-2008112078 A2 | 9/2008 |
| WO | WO-2008144693 A1 | 11/2008 |
| WO | WO-2008144695 A1 | 11/2008 |
| WO | WO-2008144697 A1 | 11/2008 |
| WO | WO-2008144698 A1 | 11/2008 |
| WO | WO-2008153689 A1 | 12/2008 |
| WO | WO-2008153819 A1 | 12/2008 |
| WO | WO-2009016636 A2 | 2/2009 |
| WO | WO-2009032399 A1 | 3/2009 |
| WO | WO-2009032400 A1 | 3/2009 |
| WO | WO-2009035759 A1 | 3/2009 |
| WO | WO-2009088983 A2 | 7/2009 |
| WO | WO-2009089028 A2 | 7/2009 |
| WO | WO-2009089029 A2 | 7/2009 |
| WO | WO-2011068648 A2 | 6/2011 |
| WO | WO-2013016363 A2 | 1/2013 |
| WO | WO-2013184896 A1 | 12/2013 |

OTHER PUBLICATIONS

Bott, et al., "Impact of Smoking on the Metabolic Action of Subcutaneous Regular Insulin in Type 2 Diabetic Patients," Horm. Metab. Res., vol. 37, 2005, pp. 445-449.

Chase, et at., "The Use of Insulin Pumps With Meal Bolus Alarms in Children With Type 1 Diabetes to Improve Glycemic Control," Diabetes Carem, vol. 29, No. 5, May 2006, pp. 1012-1015.

Communication dated Apr. 10, 2017 for Chinese Application No. 201080063326.9, 13 pages.

"Compare Insulin Pump for Diabetes," Printed from www.diabetesnet.com/diabetes-technology/insulin-pump-models.php, Jun. 18, 2009, 4 pages.

(56) References Cited

OTHER PUBLICATIONS

Decision of Rejection dated May 15, 2015 for Japanese Application No. 2012-542037, 4 pages.
Diamant B, "Subcutaneous Absorption of Insulin in Insulin—Dependent Diavetic patients. Influence of Species Physico-Chemical properties of Insulin and Physiological factors," Danish Medical Bulletin, Hildebrandt, Aug. 1991, 10 pages.
European Search Report for European Application No. 10834926.7, dated Apr. 14, 2015, 9 pages.
European Search Report for European Application No. 15168432.1, dated Sep. 8, 2015, 9 pages.
Examination Decision of the Patent Reexamination Board dated Mar. 1, 2018 for Chinese Application No. 201080063326.9, 17 pages.
Final Rejection dated Apr. 4, 2016 for Chinese Application No. 201080063326.9, 10 pages.
International Preliminary Report on Patentability for Application No. PCT/US2010/056233, dated Jun. 5, 2012, 6 pages.
International Search Report and Written Opinion for PCT Application No. PCT/US09/00107 dated May 4, 2009, 9 pages.
International Search Report and Written Opinion for PCT Application No. PCT/US2007/022004 dated Oct. 9, 2008, 11 pages.
International Search Report and Written Opinion for PCT Application No. PCT/US2007/022046 dated Mar. 7, 2008, 8 pages.
International Search Report and Written Opinion for PCT Application No. PCT/US2007/022047 dated Mar. 7, 2008, 10 pagges.
International Search Report and Written Opinion for PCT Application No. PCT/US2007/022048 dated Mar. 7, 2008, 12 pages.
International Search Report and Written Opinion for PCT Application No. PCT/US2007/022049 dated Mar. 7, 2008, 8 pages.
International Search Report and Written Opinion for PCT Application No. PCT/US2007/022050 dated Mar. 7, 2008, 10 pages.
International Search Report and Written Opinion for PCT Application No. PCT/US2007/022051 dated Mar. 7, 2008, 9 pages.
International Search Report and Written Opinion for PCT Application No. PCT/US2007/022052 dated May 11, 2007, 8 pages.
International Search Report and Written Opinion for PCT Application No. PCT/US2007/024423 dated May 19, 2008, 12 pages.
International Search Report and Written Opinion for PCT Application No. PCT/US2007/024424 dated Mar. 6, 2009, 8 pages.
International Search Report and Written Opinion for PCT Application No. PCT/US2008/002536 dated Sep. 4, 2008, 12 pages.
International Search Report and Written Opinion for PCT Application No. PCT/US2008/006449 dated Oct. 10, 2008, 17 pages.
International Search Report and Written Opinion for PCT Application No. PCT/US2008/006801 dated Oct. 30, 2008, 17 pages.
International Search Report and Written Opinion for PCT Application No. PCT/US2009/000034 dated May 27, 2009, 11 pages.
International Search Report and Written Opinion for PCT Application No. PCT/US2009/000106 dated May 13, 2009, 11 pages.
International Search Report and Written Opinion for PCT Application No. PCT/US2010/056233 dated Aug. 31, 2011, 3 pages.
International Search Report and Written Opinion for PCT Application No. PCT/US2014/021109 dated Jun. 5, 2014, 13 pages.
International Search Report and Written Opinion for PCT Application No. PCT/US2014/021318 dated May 7, 2014, 10 pages.
International Search Report and Written Opinion for PCT Application No. PCT/US2015/042881 dated Nov. 11, 2015, 11 pages.
Lehmann, et al., "Combining rule-based reasoning and mathematical modeling in diabetes care," Artificial Intelligence in Medicine, vol. 6, 1994, pp. 137-160.
Notice of Re-examination dated Oct. 16, 2017 for Chinese Application No. 201080063326.9, 10 pages.
Office Action dated Aug. 11, 2010 for European Application No. 07852760.3, 7 pages.
Office Action dated May 25, 2010 for European Application No. 08779626.4, 7 pages.
Office Action dated Apr. 7, 2010 for European Application No. 08767934.6, 3 pages.
Office Action dated Dec. 6, 2016 for Japanese Application No. 2012-542037, 3 pages.
Office Action dated Jan. 27, 2014 for Chinese Application No. 201080063326.9, 17 pages.
Office Action dated Jul. 21, 2015 for Chinese Application No. 201080063326.9, 8 pages.
Office Action dated Oct. 22, 2014 for Chinese Application No. 201080063326.9, 8 pages.
Office Action dated Sep. 10, 2013 for Canadian Application No. 2782673, 3 pages.
Office Action dated Sep. 2, 2014 for Japanese Application No. 2012542037, 8 pages.
Plougmann, et al., " DiasNet—a diabetes advisory system for communication and education via the internet," International Journal of Medical Informatics, vol. 26, 2001, pp. 319-330.
Puckett, et al., "A model for multiple subcutaneous insulin injections developed from individual diabetic patient data," vol. 269, 1995, p. E1115-E1124.
Smith Medical MD Inc., "Deltec Cozmo, Personalized Insulin Pump, Starting Guide," http://web.archive.org/web/20041207133223/http://www.cozmore.com/Library/-upload/starting.sub.--guide.sub.--032004.pdf, XP002497833, Dec. 7, 2004, pp. 1-83.
International Preliminary Report on Patentabilityfor PCT Application No. PCT/US2010/056226 dated Jun. 14, 2012, 6 pages.
Stapel E., "Converting Between Decimals, Fractions, and Percents," Purplemath, 2006, 9 pages, Available at http://www.purplemath.com/modules/percents2.htm, 2006.
Trajanoski, et al., "Pharmacokinetic Model for the Absorption of Subcutaneously Injected Soluble Insulin and Monomeric Insulin Analogues," Biomedizinische Technik, vol. 38, No. 9. Sep. 1, 1993, 8 pages.
U.S. Appl. No. 11/523,794, filed Sep. 18, 2006, 331 pages; Inventor: Moubayed.
Wach, et al., "Numerical Approximation of Mathematical Model for Absorption of Subcutaneously Injected Insulin," Med & Biol. Eng & comput., vol. 33, 1995, pp. 18-23.
Walsh, et al., "Diabetes Technology—Concept 1: Super Bolus," available at Diabetes Technology-Concept 1: Super Bolus available at http://www.diabetesnet.com/diabetes.sub.--technology/super.sub.--bolus.ph-p>, Sep. 17, 2007, 3 pages.
Walsh J., et al., "Select & Test Your Correction Factor," Pumping Insulin, Fourth Edition, Chapter 13, 2006, 10 pages.
Walsh J., et al., "Select & Test Your Basal Rates," Pumping Insulin, Fourth Edition, Chapter 2006, 30 pages.
Walsh J., et al., "Select and Test Your Carb Factor," Pumping Insulin, Fourth Edition, Chapter 2006, 32 pages.
Walsh J., et al., "Pumping Insulin: Everything you need for Success on a Smart insulin Pump," Torrey Pines Press, San Diego, ISBN 1-884804-86-1, 2006, 3 pages.
wikipedia.com, "Wikipedia's definition for "basal rate"," printed from wikipedia.com on Jun. 12, 2009, 1 page.
Wilinska, et al., "Insulin Kinetics in Type-1 Diabetes: Continuous and Bolus Delivery of Rapid Acting Insulin," IEEE Transactions on Biomedical Engineering, vol. 52, No. 1, Jan. 2005, pp. 3-12.
Application and File history for U.S. Appl. No. 11/626,653, filed Jan. 24, 2007. Inventors: Blomquist et al.
Application and File history for U.S. Appl. No. 12/720,306, filed Mar. 9, 2010. Inventors: Blomquist et al.
Application and File history for U.S. Appl. No. 11/753,420, filed May 24, 2007. Inventors: Blomquist.
Application and File history for U.S. Appl. No. 12/774,991, filed May 6, 2010. Inventors: Blomquist.
Application and File history for U.S. Appl. No. 13/530,404, filed Jun. 22, 2012. Inventors: Blomquist.
Application and File history for U.S. Appl. No. 14/684,495, filed Apr. 13, 2015. Inventors: Blomquist.
Application and File history for U.S. Appl. No. 14/962,635, filed Dec. 8, 2015. Inventors: Blomquist.
Application and File history for U.S. Appl. No. 11/755,480, filed May 30, 2007. Inventors: Blomquist.
Application and File history for U.S. Appl. No. 13/465,570, filed May 7, 2012. Inventors: Blomquist.

(56) References Cited

OTHER PUBLICATIONS

Application and File history for U.S. Appl. No. 14/187,414, filed Feb. 24, 2014. Inventors: Blomquist.
Application and File history for U.S. Appl. No. 15/830,415, filed Dec. 4, 2017. Inventors: Blomquist.
Application and File history for U.S. Appl. No. 11/970,232, filed Jan. 7, 2008. Inventors: Blomquist et al.
Application and File history for U.S. Appl. No. 12/908,218, filed Oct. 20, 2010. Inventors: Blomquist et al.
Application and File history for U.S. Appl. No. 13/481,302, filed May 25, 2012. Inventors: Blomquist et al.
Application and File history for U.S. Appl. No. 14/455,508, filed Aug. 8, 2014. Inventors: Blomquist et al.
Application and File history for U.S. Appl. No. 14/797,652, filed Jul. 13, 2015. Inventors: Blomquist et al.
Application and File history for U.S. Appl. No. 12/631,076, filed Dec. 4, 2009. Inventors: DeBelser et al.
Application and File history for U.S. Appl. No. 14/525,579, filed Oct. 28, 2014. Inventors: DeBelser et al.
Communication for European Application No. 10834926.7, dated Dec. 7, 2018, pages.
Office Action dated Apr. 26, 2020 for Chinese Application No. 201810596660.9, 20 pages.

\* cited by examiner

ADVANCED STEP THERAPY DELIVERY FOR AN AMBULATORY INFUSION PUMP AND SYSTEM

RELATED APPLICATION

This application is a continuation of application Ser. No. 14/525,579 filed Oct. 28, 2014, which in turn is a continuation of application Ser. No. 12/631,076 filed Dec. 4, 2009, now U.S. Pat. No. 8,882,701 issued Nov. 11, 2014, each of which is hereby fully incorporated herein by reference.

TECHNICAL FIELD

The invention relates generally to ambulatory infusion pumps and more specifically to step therapy delivery by an ambulatory infusion pump.

BACKGROUND

Ambulatory infusion pumps are useful for providing a variety of drug therapies. Ambulatory pumps can be particularly beneficial for therapies which must be delivered over an extended period of time.

One such therapy is intravenous immunoglobulin (IVIG). IVIG is used primarily to treat immune deficiencies, inflammatory and autoimmune disorders, and acute infections. Patients receiving IVIG therapies typically need to build up a tolerance to the IVIG during delivery, meaning that IVIG is initially administered at a low rate and, as the infusion time progresses, the rate is gradually increased to a steady state or "plateau" rate that is maintained until the prescribed amount of IVIG has been delivered to the patient. IVIG is not the only therapy that utilizes this type of delivery profile.

While some conventional infusion pumps can accommodate such a delivery profile, setting up and programming the profiles on the pumps is complicated and time-consuming. Further, many conventional pumps use spreadsheet-based profiles that cannot be adjusted or customized, either prior to infusion to accommodate the needs of a particular patient or during infusion if a patient is not tolerating the delivered drug and needs to decrease the rate of infusion on demand.

SUMMARY OF THE INVENTION

Embodiments relate to systems, methods and devices for defining a step delivery function for an ambulatory infusion pump and delivering, by the pump, a drug according to the step delivery function.

In one embodiment, an ambulatory infusion pump comprises an infusion therapy delivery mechanism, a graphical user interface (GUI) configured to receive a plurality of parameters defining a step delivery function, the plurality of parameters comprising an initial rate, a plateau rate, a step duration, a rate increment and a total infusion volume, and a processor coupled to the therapy delivery mechanism and configured to calculate an infusion duration based on at least one of the plurality of parameters and to cause the therapy delivery mechanism to operate based on the step delivery function.

In one embodiment, a method of defining a step delivery function for an ambulatory infusion pump comprises receiving an initial rate, a plateau rate, a step duration, a rate increment and a total infusion volume, and automatically determining an infusion duration based on at least the initial rate, the plateau rate, the step duration, the rate increment and the total infusion volume.

In one embodiment, an infusion system comprises an initial rate setting, a plateau rate setting, a step duration setting, a rate increment setting, a total infusion volume setting, and an infusion duration setting that is automatically set according to the initial rate setting, the plateau setting, the step duration setting, the rate increment setting and the total infusion volume setting.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
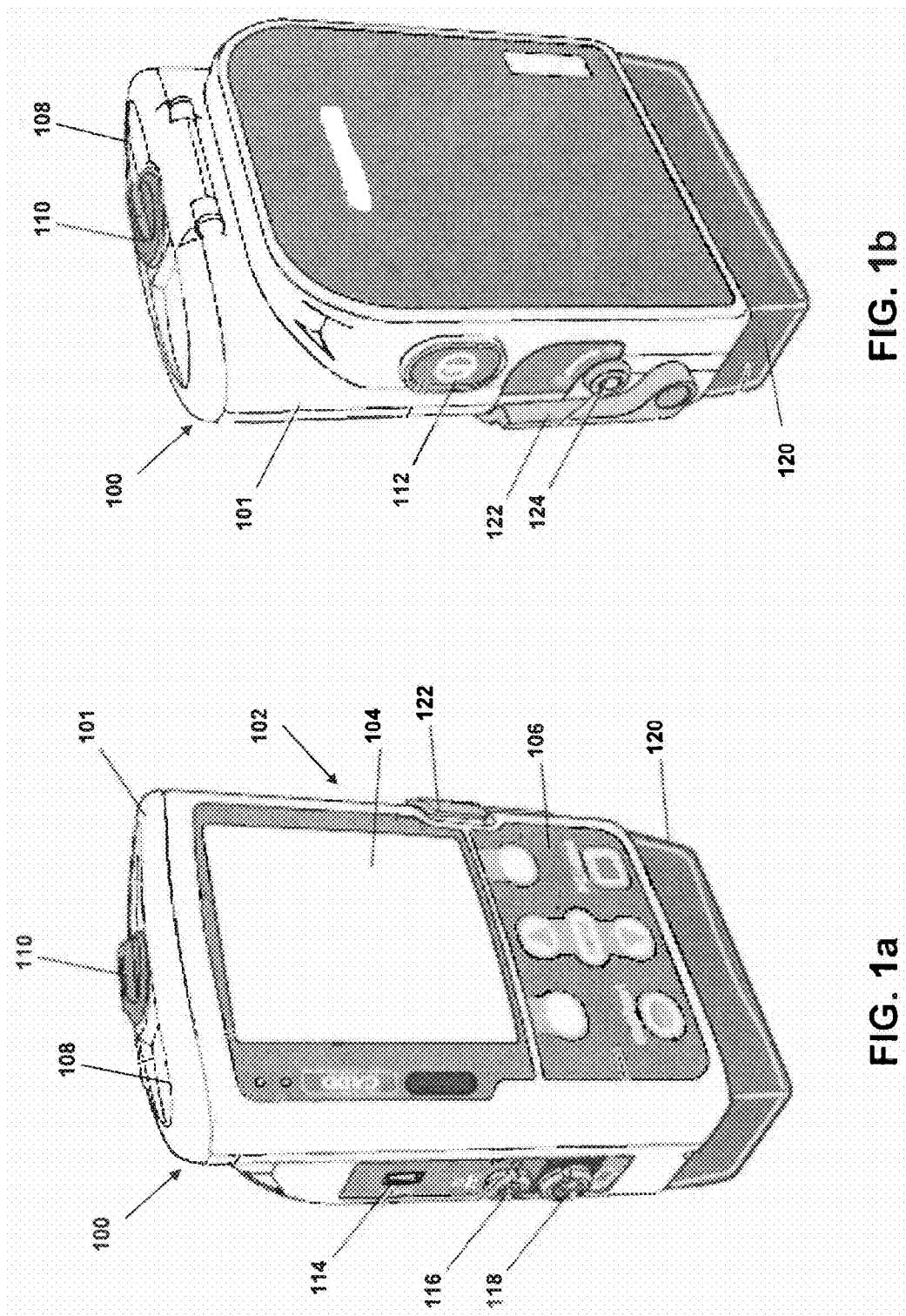
FIG. 1a is a front perspective view of an ambulatory infusion pump according to an embodiment.
FIG. 1b is a rear perspective view of an ambulatory infusion pump according to an embodiment.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Embodiments of the invention relate to a step therapy delivery system for an ambulatory infusion system. In one embodiment, the ambulatory infusion system can be a CADD-Solis® Ambulatory Infusion System from Smiths Medical ASD, Inc. The ambulatory infusion system can also be of the type disclosed in commonly owned U.S. Patent Application Pub. Nos. 2008/0065007, 2008/0065016 and 2008/0132844, assigned to Smiths Medical ASD, Inc., which are incorporated by reference herein in their entireties. In other embodiments, other infusion pumps can be used.

Figure 2:
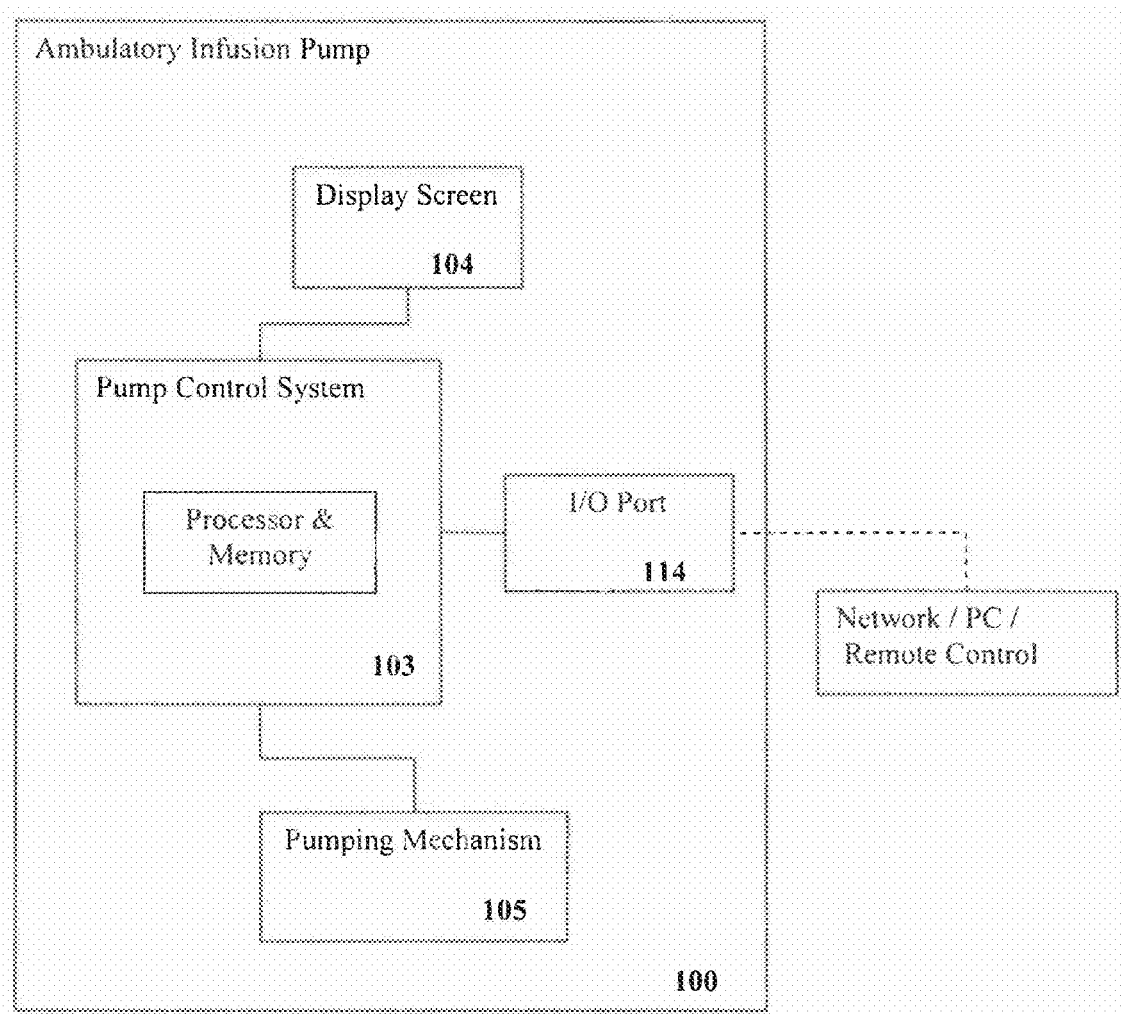
FIG. 2 is a block diagram of selected elements of ambulatory infusion pump of FIGS. 1a and 1b.

An exemplary ambulatory infusion pump 100 can provide a step delivery therapy to a patient and is depicted in FIGS. 1a and 1b, and FIG. 2. Ambulatory infusion pump 100 includes a pump control system 103 with a processor and memory programmable with selected protocols, profiles and other settings for controlling operation of a pumping mechanism 105. Ambulatory infusion pump 100 can also include a control module 101 for relaying commands to the control system 103. Control module 101 can include a user interface 102 having a display screen 104 and a control pad 106. Control module 101 can also include a battery door 108, including a knob 110 for locking and unlocking the door 108, which covers a battery compartment in which batteries for powering the pump 100 can be contained. Control module 101 can also include a power switch 112 for turning pump 100 off and on, a USB port 114, or other appropriate I/O interface, for connecting pump 100 to a computer having software designed to interface with pump 100, an AC power jack 116 for connecting an AC power cord for powering pump 100, and a remote dose cord jack 118 for connecting a remote dose cord that provides an alternative way to activate patient-controlled dosing.

Infusion pump 100 can further include a replaceable cassette 120 connected to control module 101. In one embodiment, cassette 120 includes a reservoir containing the medication that is to be delivered to the patient. Tubing can extend from the cassette 120 and communicate with an infusion set or catheter to deliver the medication to the patient. The control module 101 can be used to control the flow of medication from the cassette. One example of such a cassette is the CADD® Medication Cassette Reservoir from Smiths Medical ASD, Inc., though other cassettes can be used in other embodiments. In another embodiment, cassette 120 can include tubing that interfaces with a remote medication reservoir such as an IV bag. Tubing can extend from the reservoir to the cassette and then to an infusion set or catheter, and flow of medication through the tubing can be controlled with control module 101. One example of such a set is part of the CADD® Administration Set from Smiths Medical ASD, Inc.

A step delivery can be used with various drug therapies, though in one embodiment a step function for pump 100 is tailored for intravenous immunoglobulin (IVIG) therapies. IVIG therapies typically require a period of initial dosing. Once complete, an increased dosage (or "step up") can be periodically delivered. Step delivery allows the infusion of a drug at an initial rate with step increases to a plateau rate. If patient tolerance is not successful at any rate, the treatment can be scaled back or stopped on demand. Multiple steps down can be applied, reducing the dosage rate down to any previous rate. In other embodiments, a step delivery profile can be suitable for nutritional and other therapies.

The step delivery profile of the pump 100 is selectively defined by parameters provided to the pump control system 103. In one embodiment: an initial rate, a plateau rate, a step duration, a rate (step) increase or increment, and a total infusion volume, as shown by diagram 130 depicted in FIG. 3 can be provided. An additional parameter, infusion duration 132, does not have to be provided by a user in an embodiment; rather, infusion duration 132 is automatically calculated based upon one or more of the other parameters in an embodiment. For example, a minimum programmable infusion duration is defined by a combination of the infusion volume, step duration and various rates of delivery. In an embodiment, pump 100 provides a calculated infusion duration 132 after the other parameters are programmed. In an embodiment, pump control system 103 also calculates the total number of steps necessary to transition from the initial rate to the plateau rate based on one or more programmed parameters. During delivery of a step delivery profile, a user may "step down" a delivery rate. In one embodiment, pump 100 automatically adjusts one or more parameters of the programmed step delivery profile to accommodate the departure from the initial program. This can include adjusting, i.e., lengthening, the total infusion duration automatically. In an additional embodiment, an optional KVO ("keep vein open") rate 134 is provided, which allows delivery of a minimal amount of drug to help maintain catheter patency. The KVO rate 134 can be considered by the pump 100 in determining a calculated infusion duration 132 in one embodiment. Thus, in various embodiments, the step calculation function of the pump control system 103 calculates a single total infusion duration 132 based on the entered parameters and therefore does not need minimum and maximum duration parameters.

Figures 3, 4:
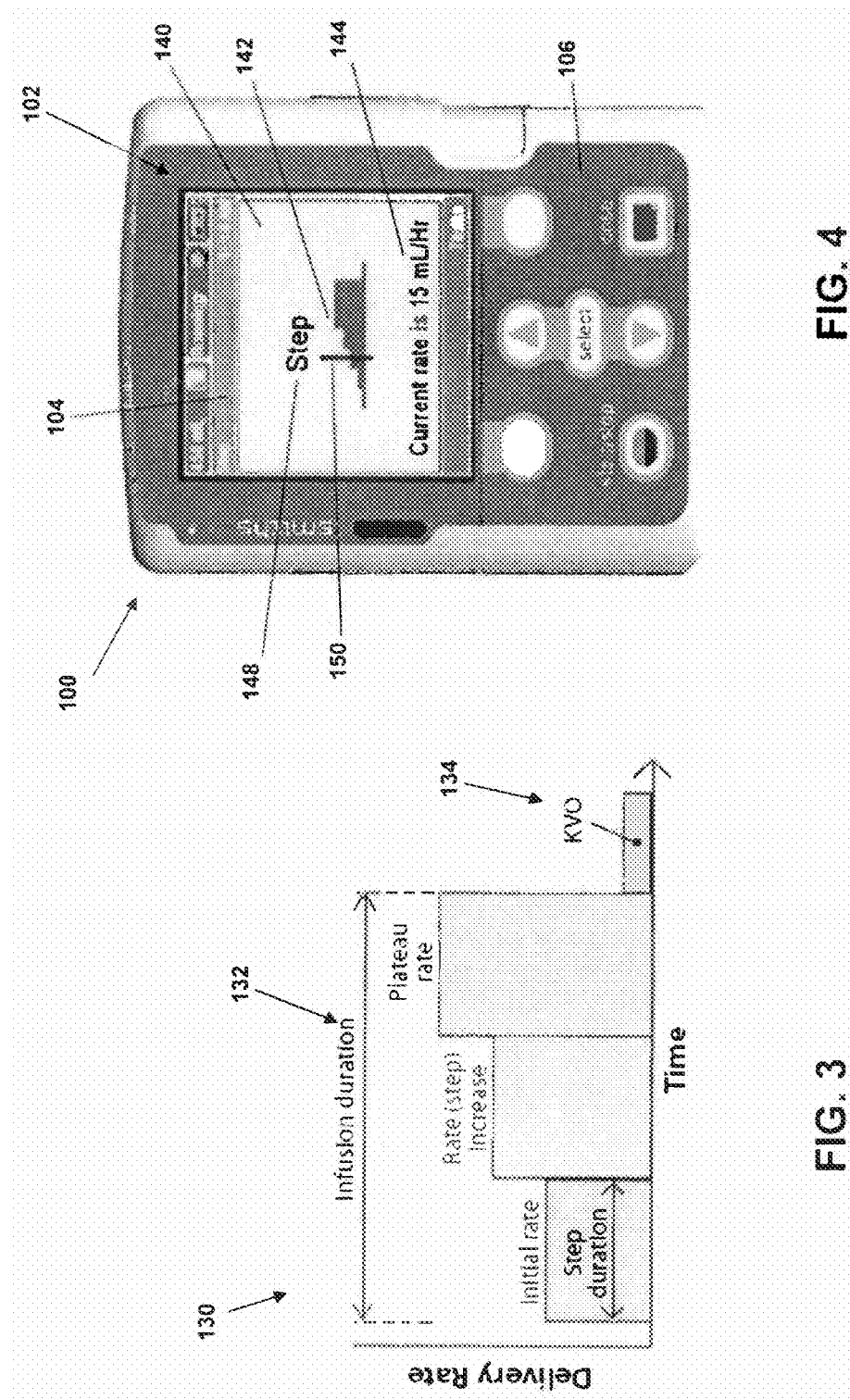
FIG. 3 is a graphical representation of the various parameters of therapy delivery according to an embodiment.
FIG. 4 is a view of a delivery profile graphic provided by a ambulatory infusion pump graphical user interface (GUI) according to an embodiment.

As depicted in FIG. 4, the display screen 104 of the pump 100 provides a graphical user interface (GUI) 140 during operation. An example delivery profile graphic 142 when the pump 100 is started is shown on the display screen 104. The information displayed on the GUI 140 may vary but can include information of most interest to a user or patient during delivery, such as the current rate of delivery 144, the mode of operation 148, and any other appropriate status indications. In the embodiment of FIG. 4, the pump 100 is in step mode 148. During infusion, the GUI 140 can present an indicator graphic 150, along with the delivery profile graphic 142, illustrating how far the patient's treatment has progressed. In the example shown, the therapy delivery is in the second of four stages, at a rate of fifteen mL per hour.

Figure 5:
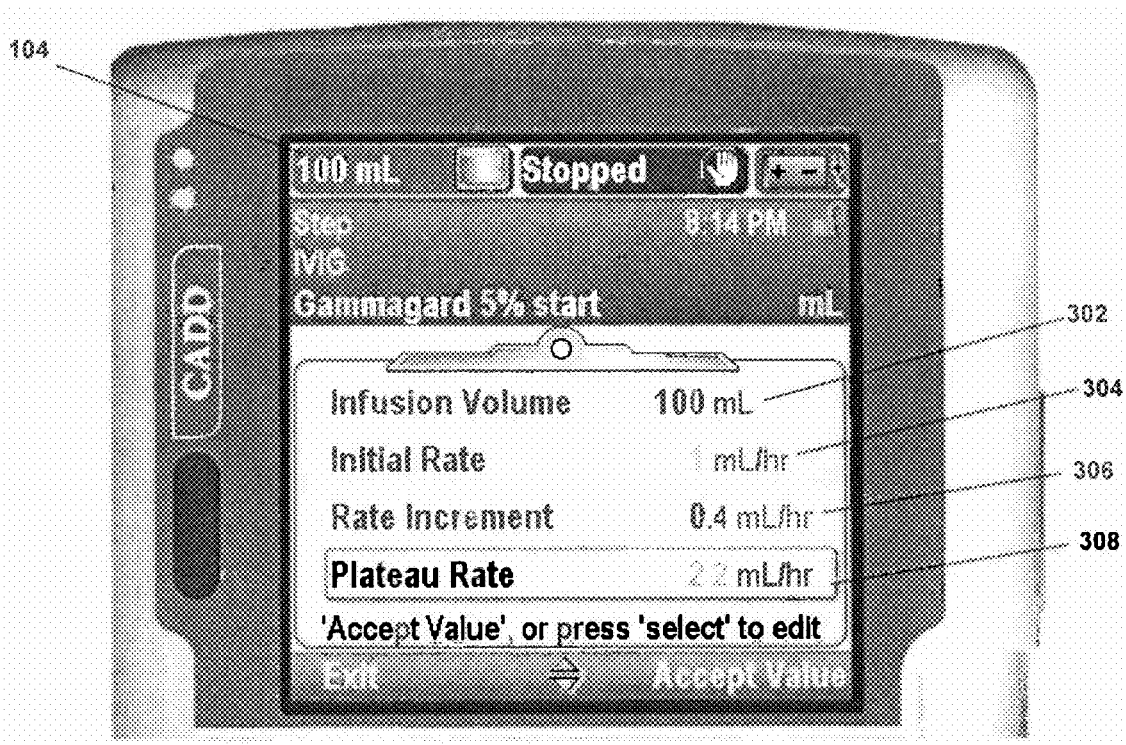
FIG. 5 is a view of a menu provided by a GUI according to an embodiment.
Figure 6:
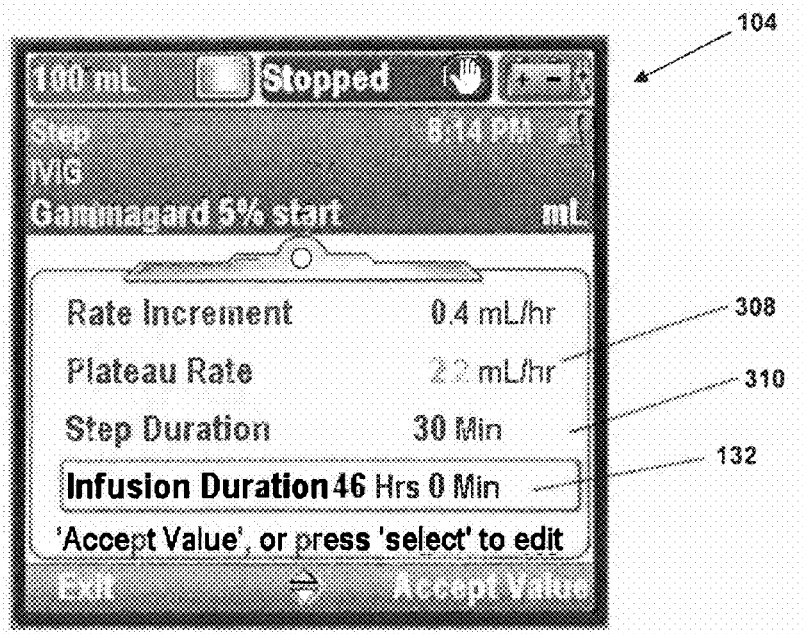
FIG. 6 is a view of a menu provided by a GUI according to an embodiment.
Figure 7:
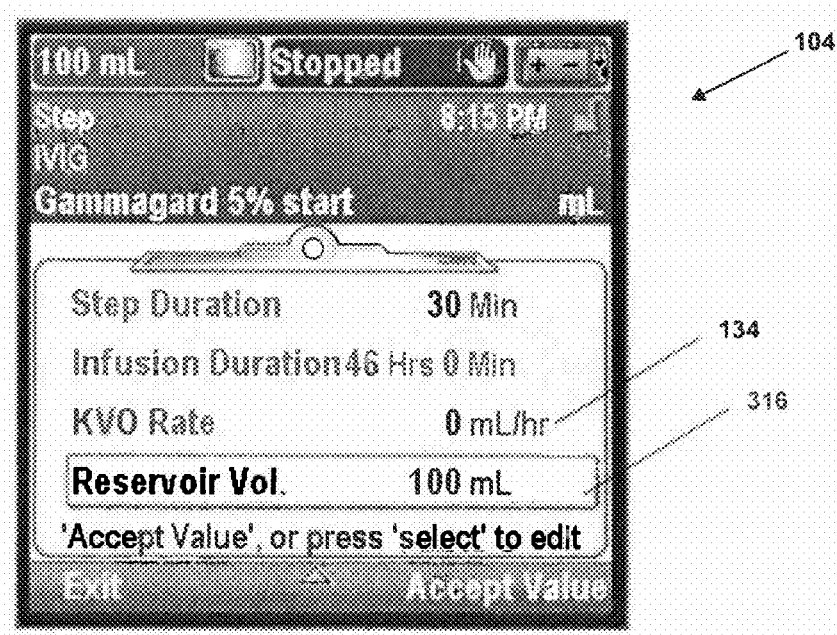
FIG. 7 is a view of a menu provided by a GUI according to an embodiment.

As depicted in FIGS. 5-7, programming screens present a user with an interface to input the parameters defining the therapy delivery. The user, potentially a clinician or home health-care provider, can enter the dosage parameters provided by a prescribing physician. The user can also utilize the interface to determine the status of treatment and reduce the dosage rate if necessary. In one embodiment, certain parameters or profiles specific to a patient can be retained or stored by pump 100, or by a related computer system, to facilitate quicker, more convenient, and safer use of pump 100; in particular to avoid programming errors or delivery of a profile intended for another patient. In other embodiments, individual or multiple profiles can be programmed using a related computer system and software, and then downloaded to one or more pumps 100 for patient therapy.

FIG. 5 depicts a programmed infusion volume 302 of one hundred mL. Infusion volume 302 is the total volume of drug or therapy fluid to be delivered according to a prescription. Entering a new infusion volume 302 resets the configured infusion profile so that therapy delivery starts at the beginning of a new infusion duration 132 for the patient.

Initial Rate 304 is the rate at which therapy delivery will begin. This also can be the minimum delivery rate that a user can "step down" to. Rate Increment 306 is the amount of desired amount of medication delivery increase for each step.

Plateau Rate 308 is the maximum rate at which the pump 100 is to deliver the medication. The pump 100 begins at the initial rate, and increases by the rate increment until the plateau rate 308 is reached, absent a step-down indication from a user. The pump 100 can run at this rate until the reservoir volume reaches zero or when the predetermined infusion volume 302 is delivered. The pump control system 103 can calculate the rate of delivery that will occur during the plateau portion of the infusion profile based on the infusion volume and infusion duration, depending on the desired parameters. The pump 100 can be pre-configured with a maximum allowable rate. For example, a rate above 250 mL/hr can require a high volume therapy administration set. A low volume therapy administration set would not accept parameters that resulted in a plateau rate 308 above 250 mL/hr.

Step Duration 310 is the length of time programmed for each step during medication delivery. This time period corresponds to the duration of each step's therapy delivery period. The sum of all step duration 310 periods for each step required to reach the plateau rate 308, as well as the length of the plateau period, is then equal to the total infusion duration 132 to deliver the full infusion volume 302.

Infusion duration 132 is the time required to deliver the total infusion volume 302. In an embodiment, infusion duration 132 is calculated by the pump 100 based on one or more of the initial values programmed for the patient-specific parameters: infusion volume 302, initial rate 304, rate increment 306, plateau rate 308, and step duration 310. The user does not need to provide a duration value in one embodiment. Once the parameters are entered, the pump control system 103 calculates infusion duration 132.

Reservoir Vol. 316 is the volume of fluid contained in the reservoir or cassette 120. The administrator can configure a standard reservoir volume 316 which allows the reservoir volume 316 setting to be quickly reset to that configured value. As shown in FIG. 7, a clinician can adjust the reservoir volume 316 to another amount, resetting the reservoir volume. In one embodiment, the reservoir volume 316 cannot be set to less than the programmed infusion volume 302. The reservoir volume 316 value decreases as the pumping mechanism is primed or delivers fluid.

The KVO Rate, or "keep vein open" rate, 134 is optional. It allows delivery of a minimal amount of a drug to help maintain catheter patency. If a delayed start is programmed, the KVO rate 134 is active during the initial delay. It is also active after the infusion profile is complete if the reservoir volume 316 programmed is greater than the infusion volume 302. If a KVO delivery rate 134 is intended at the end of the infusion profile, the reservoir volume must be larger than the infusion volume so that automatic KVO delivery may occur. The KVO delivery rate 134 continues until the reservoir volume 316 reaches zero mL or until the pumping mechanism is stopped.

Figure 8:
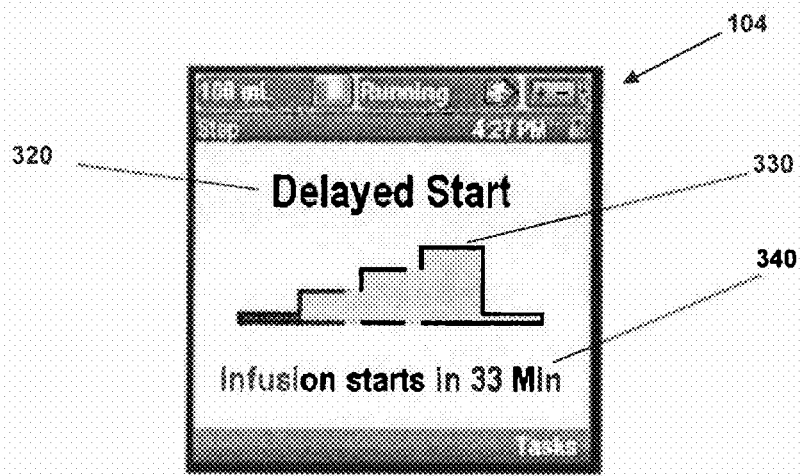
FIG. 8 is a view of a delayed start graphic provided by a GUI according to an embodiment.

The user can also program a delayed start time (not depicted) that is the time that the next infusion delivery will begin. It is displayed only if a delayed start is programmed. FIG. 8 depicts pump 100 in delayed start mode 320. The graphic 330 indicates that the pump 100 is in the first stage of minimum therapy delivery. The time 340 until the delivery of the therapy increases to the initial rate 304 is also displayed and periodically updated on display screen 104.

Figure 9:
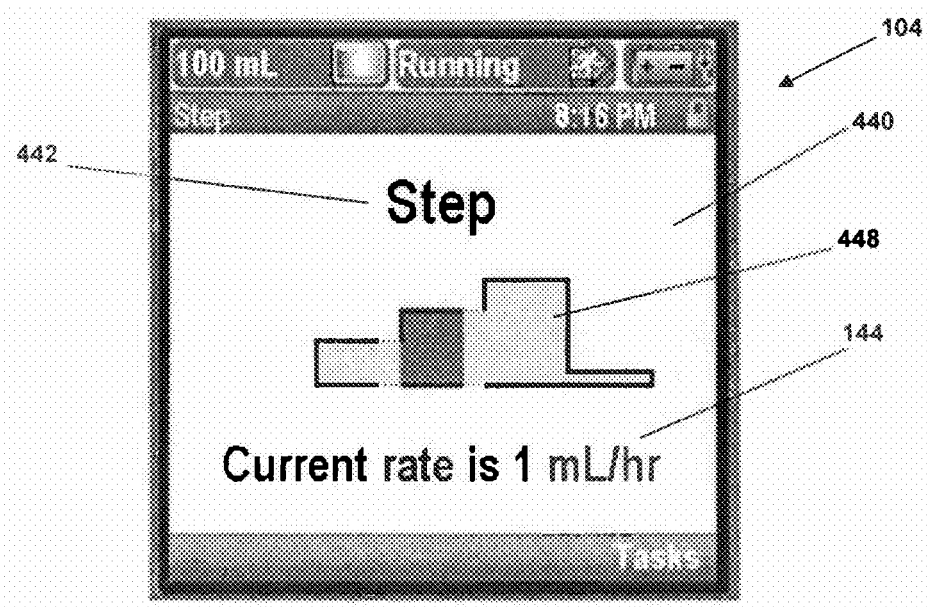
FIG. 9 is a view of a delivery profile graphic provided by a GUI according to an embodiment.
Figure 10:
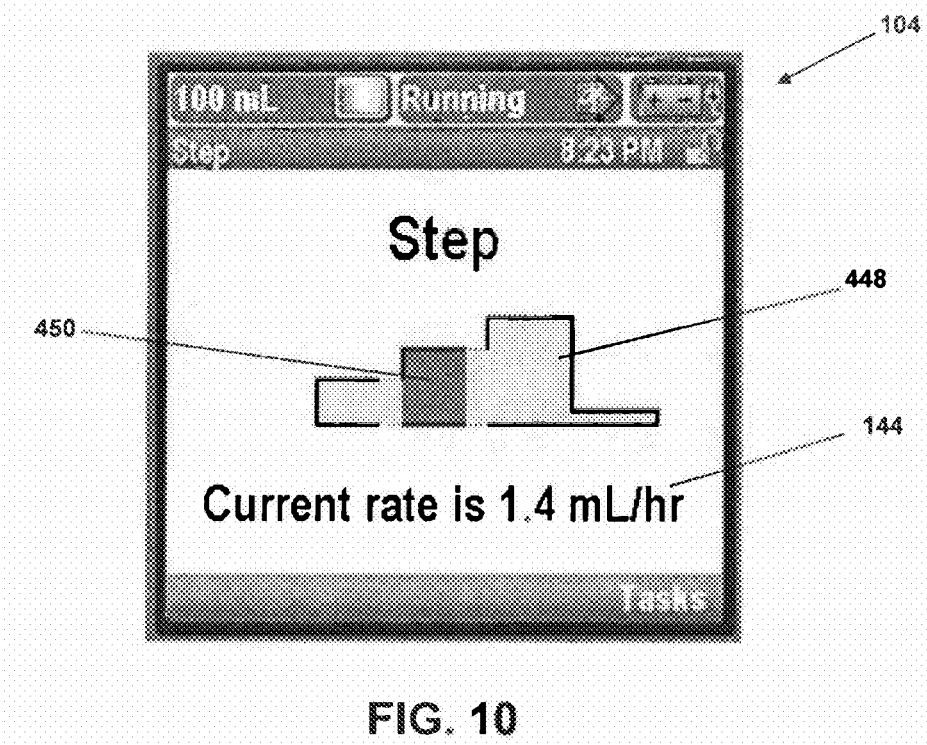
FIG. 10 is a view of a delivery profile graphic provided by a GUI according to an embodiment.

FIGS. 9 and 10 depict two examples of the display screen 104 of the pump 100 presenting a running status screen 440 indicating the current rate of delivery 144 and that the pump 100 is in the step mode 442 of operation. The running status screen 440 includes an example of a step delivery icon 448 that includes a status bar 450. The location of the status bar 450 in the middle of the delivery icon 448 indicates that the pump 100 is at an intermediate step in the therapy delivery. The pump 100 is delivering a medication at a current rate 144 that is less than the plateau rate 308.

Figure 11:
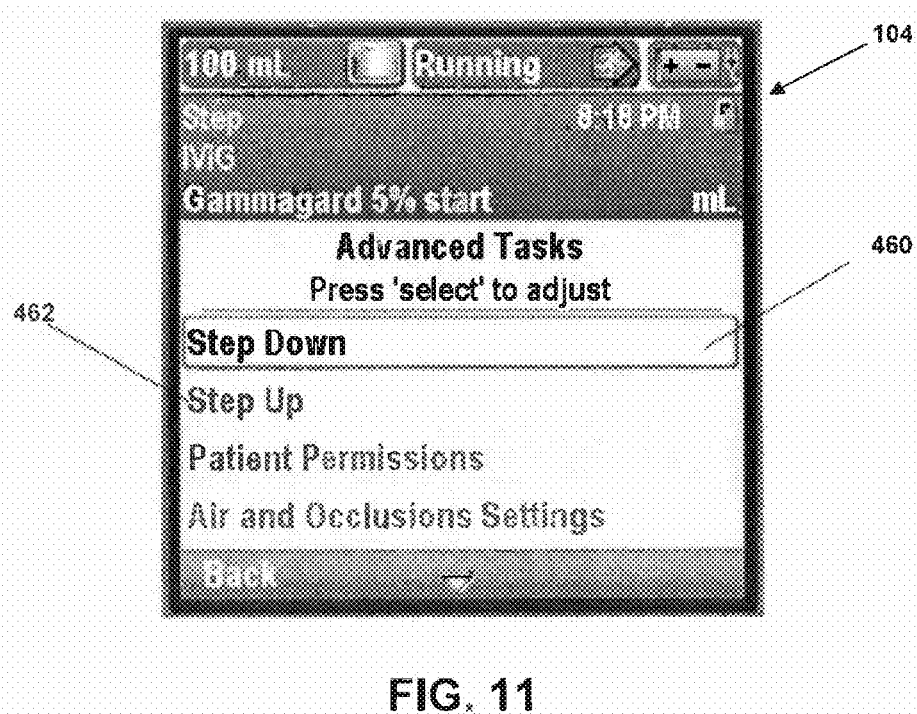
FIG. 11 is a view of a menu provided by a GUI according to an embodiment.

FIG. 11 depicts GUI menu commands Step Down 460 and Step Up 462 from the advanced tasks menu that can be used to change the actual current step, i.e. the infusion duration by reducing or increasing the rate of therapy administration. The step up and step down procedures are described below. After the selection of the Step Down 460 or Step Up 462 commands, the infusion duration time is automatically recalculated in one embodiment. The displayed total infusion duration 132 value can change to reflect the new setting, or it can be configured to display the initial time value and indicate that a change has been directed that deviated from the original configuration.

Figure 12A:
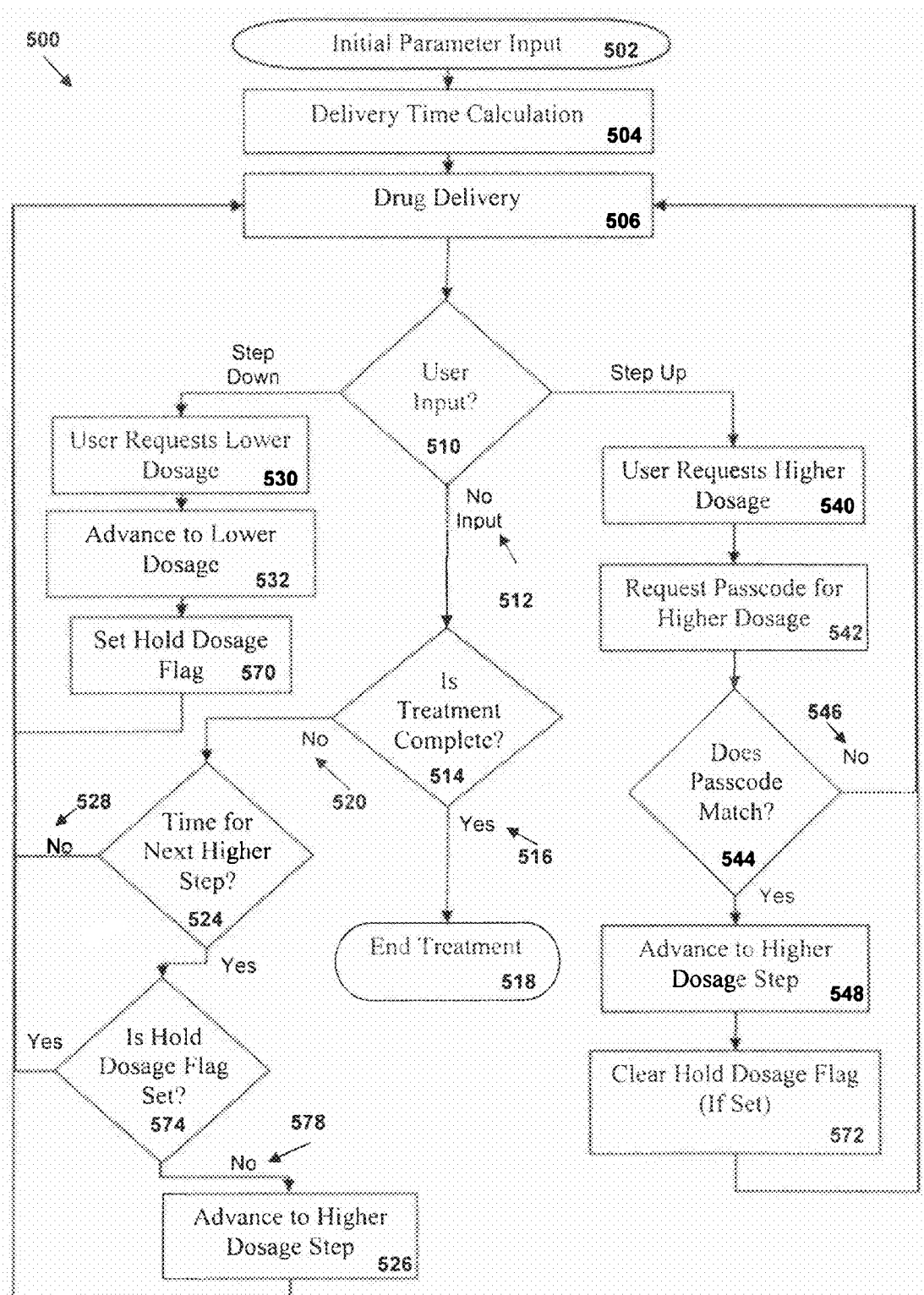
FIG. 12a is a flowchart of a step therapy delivery system according to an embodiment.
Figure 12B:
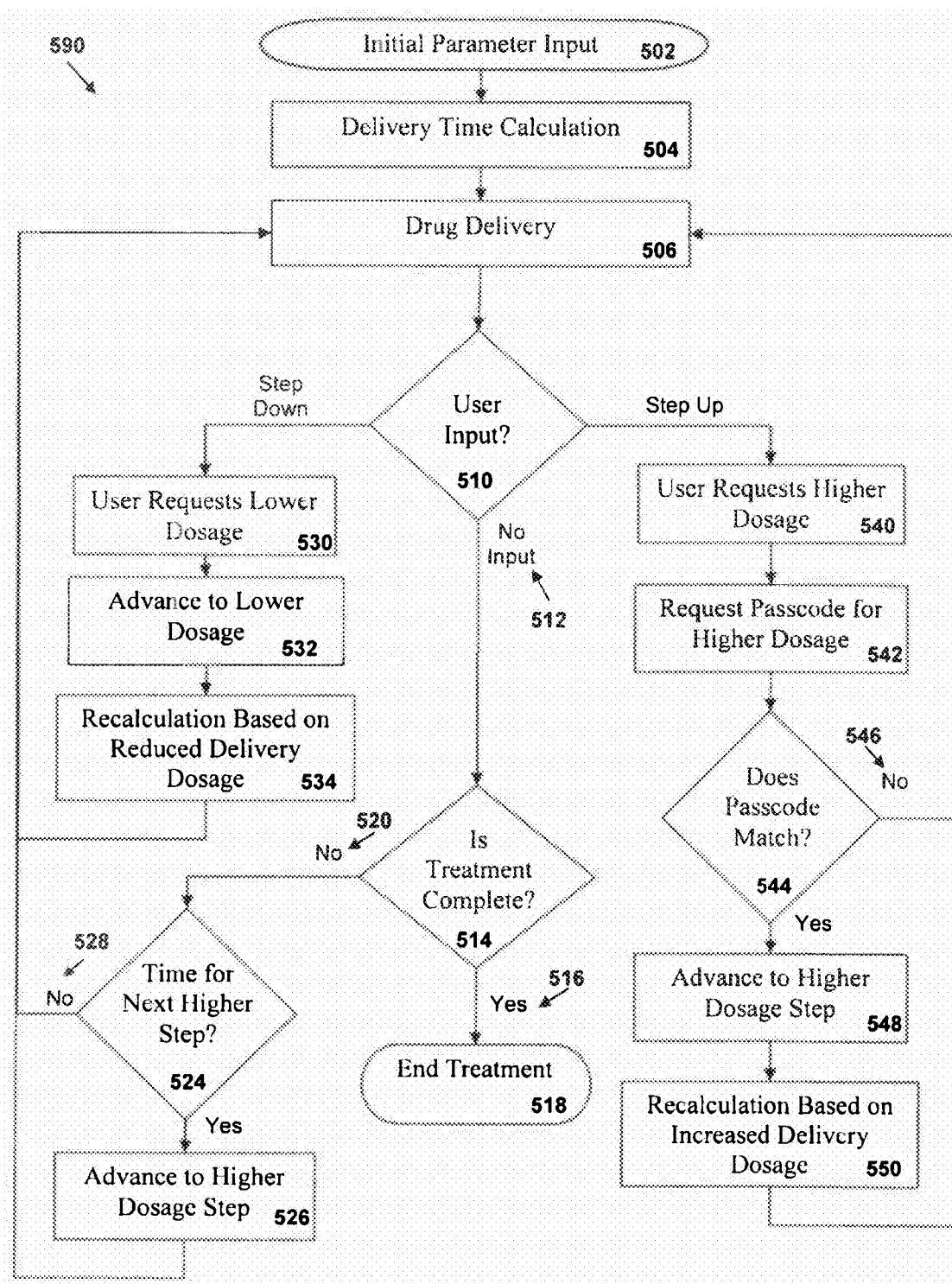
FIG. 12b is a flowchart of a step therapy delivery system according to an embodiment.

FIGS. 12a and 12b depict flowcharts 500 and 590 of exemplary embodiments of a step therapy protocol for an ambulatory infusion system. Initially, a clinician or health care provider inputs the desired parameters 502 as discussed above. Typical parameters can include total infusion volume, initial rate, rate increment, plateau rate, and step duration in an embodiment. The pump control system 103 will next calculate the initial infusion duration delivery time 504. Once the settings are confirmed by the user, the pump 100 can commence the delivery 506 by engaging the pumping mechanism of the pump 100.

The stepped delivery function of the pump 100 is interruptible, for example a patient may selectively hold at a current level rather than stepping up to the next level, or may step back to a previous lower therapy delivery level if tolerance was not achieved. During delivery, the pump 100 also provides patient convenience features, such as a notification at step up transition. The notification can come in advance of a transition such that a user can check the patient's vitals or condition prior to a transition.

The pump 100 can receive user input 510 through the GUI 140 during drug delivery 506. If there is no user input, the delivery mode 506 continues until the pump control system 103 determines that treatment is complete 516. The determination of completed treatment can be based on the delivery of the entered infusion volume 302. When the treatment is complete 520, the pumping mechanism can either be deactivated, or reduced to a KVO delivery rate 134 if configured and if reservoir volume 316 has not reached zero mL.

If treatment is not complete 520, the pump control system 103 will check to see if the step duration 310 time period has elapsed 524. If step duration 310 for the current therapy delivery period has been completed, the pump 100 will advance to the next higher dosage step 526 and increase the drug delivery 506 by the amount of the rate increment 306. The rate of drug delivery 506 is limited by the plateau rate 308. Optionally, the pump 100 can provide a notification at or before the dosage increase, or prompt the user for a confirmation to acknowledge the dosage increase before the higher dosage is delivered. The pump 100 can continue with drug delivery as before unless prompted by the user 510 or treatment is completed 516. If the step duration 310 has not elapsed 528, the pump 100 will continue with drug delivery 506.

If the user inputs a step down command requesting a lower dosage 530, then the pump 100 will reduce the therapy to the lower dosage 532 by the amount of one dosage rate increment 304. In the embodiment depicted in FIG. 12a, the pump 100 will remain at this lower drug delivery 506 stage unless requested by the user to provide a higher dosage 540 or until treatment is completed 516. The pump 100 can maintain the lower delivery rate by setting an internal hold dosage flag 570 that is checked 574 prior to advancing to a higher dosage step 526. In the embodiment of FIG. 12b, the reduction in dosage causes a recalculation 534 of the infusion duration 132 based on the new reduced delivery dosage by the pump control system 103. The user can enter multiple step down commands, reducing the dosage by one or more increments, or halting treatment completely. In an alternative embodiment, the pump 100 can prompt the user for permission to increase the dosage after another step duration 310 time period has elapsed.

If the user inputs a request for a higher dosage 540, the pump 100 can prompt the user to enter a passcode 542. The request for a passcode can be used to prevent the patient receiving treatment for increasing their dosage without supervision, or to limit the ability to increase the dosage to certain authorized individuals. Passcodes can also be used by default for any programming feature or in other situations related to the use of the pump 100. If a requested passcode does not match 546 the pump 100 remains at the current drug delivery 506 stage. If the preconfigured passcode is entered the pump 100 advances to the higher dosage stage 548 by the amount of one dosage rate increment 304. In the embodiment of FIG. 12b, the increase in dosage leads to a recalculation 550 of the infusion duration 132 based on the increased delivery dosage by the pump control system 103. In the embodiment of FIG. 12a, the hold dosage flag 570 can be cleared 572 if the user requests a higher dosage level 540. The user can enter multiple step up commands, increasing the dosage by one or more increments, up to the configured plateau rate. One skilled in the art will appreciate that other variations or combinations of the embodiments described in FIGS. 12a and 12b are possible.

Figure 13:
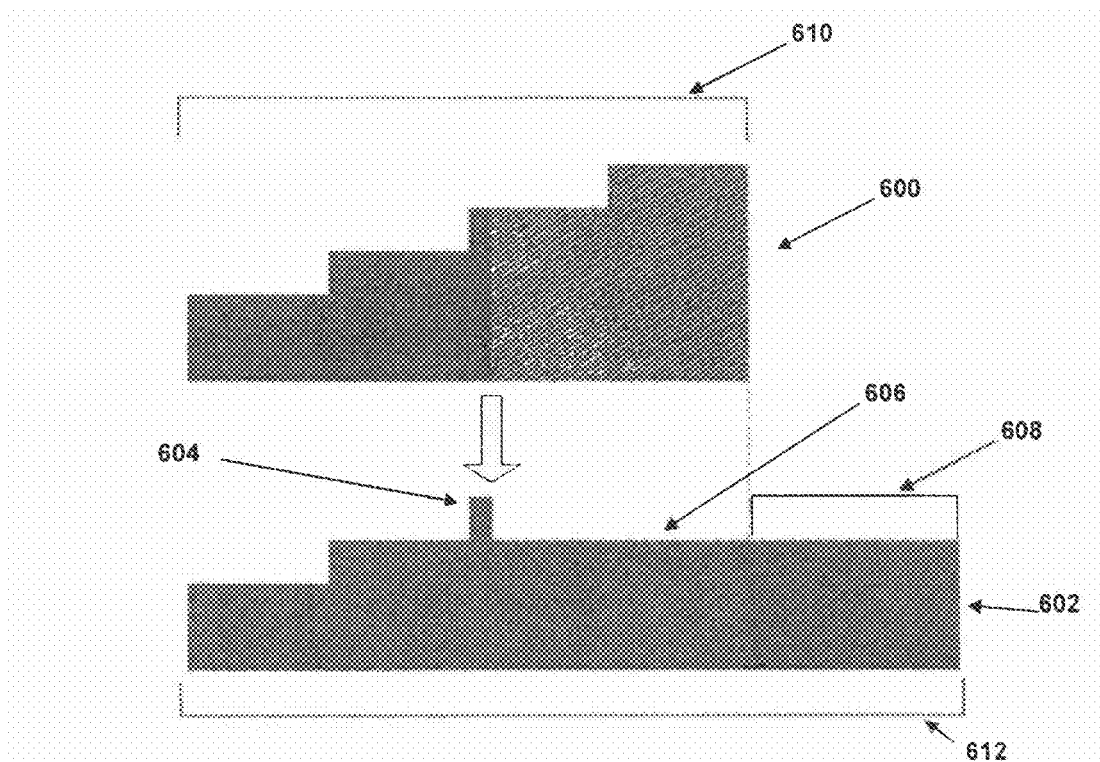
FIG. 13 is a graphical representation of therapy delivery of a directed "step down" according to an embodiment.

FIG. 13 depicts an example of an initial delivery profile 600 and a resulting delivery profile 602 after a decrease or "step down" in dosage rate. If the user experiences an adverse reaction to an increased dosage, the user can direct the pump 100 to revert back to the previous, lower, dosage level. As illustrated, the selection of the step down command option 460, on the GUI 140 of FIG. 11, decreases the therapy dosage from the current dosage 604 to the previous lower dosage 606. The decrease in dosage increases the overall therapy delivery time by an additional period 608. The additional period 608 extends the original dosage period 610 to the new dosage period 612. In this example, the previous lower dosage 606 rate is maintained for the entire new dosage period 612. No automatic increase in dosage is performed by the pump 100, though this can vary in other embodiments.

Figure 14:
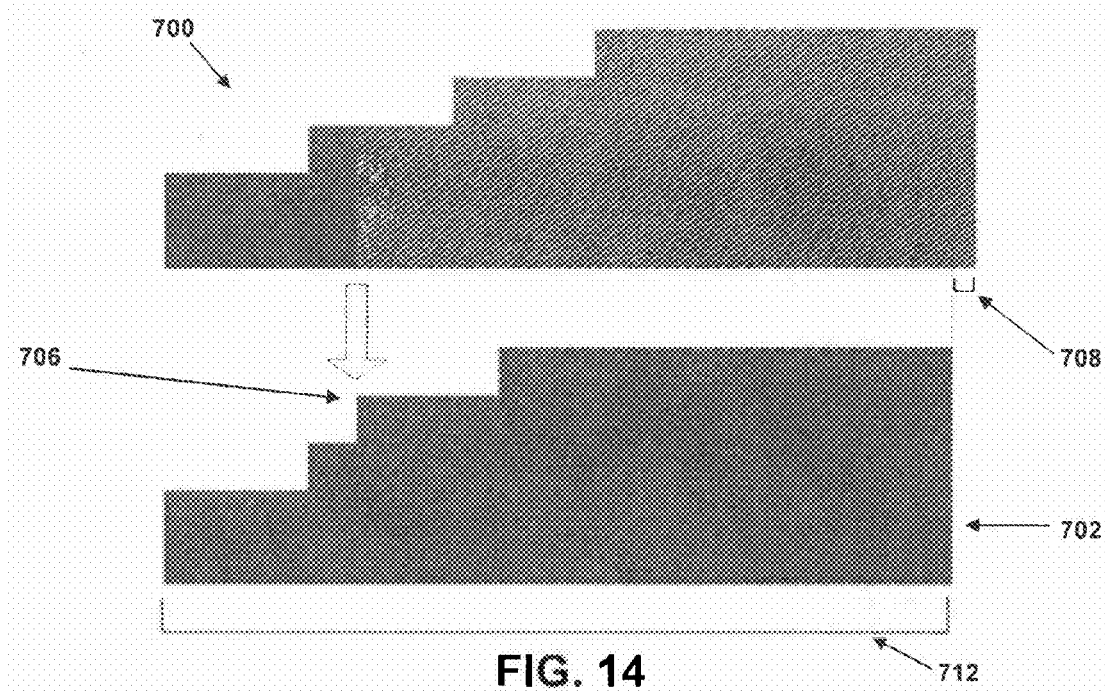
FIG. 14 is a graphical representation of therapy delivery of a directed "step up" according to an embodiment.

FIG. 14 depicts an example of an initial delivery profile 700 and a resulting delivery profile 702 after an increase or "step up" in the dosage rate. As illustrated, the step up command 462 on the GUI 140 of FIG. 11 increases the therapy dosage to the next higher dosage 706. This dosage then continues for one entire new step duration 310 regardless of how far into the current step duration 310 the pump 100 had progressed when the "step up" option was initiated. The increase in dosage rate can decrease the overall therapy delivery time by a shortened period 708. This reduces the overall therapy delivery time required to administer the full infusion volume 302.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An ambulatory infusion pump configured to deliver medicament according to a customized delivery profile that enables a patient to gradually build up a tolerance to the medicament during a therapy session, the ambulatory infusion pump comprising:
 a pump control system configured to control operation of a pumping mechanism according to one or more tolerance-building delivery rates defined by a step delivery profile; and
 a control module in communication with the pump control system, the control module including a user interface presenting a step delivery profile graphic representing a diagram graphical representation of the step delivery profile, and an indicator graphic illustrating progress along the step delivery profile during the therapy session, wherein a y-axis of the step delivery profile represents a delivery rate of the medicament, and an x-axis of the step delivery profile graphic represents time, wherein the indicator graphic moves along the x-axis of the step delivery profile graphic as the therapy session progresses, and
 wherein the ambulatory infusion pump is configured to automatically lengthen a duration of the step delivery profile and of the step delivery profile graphic presented on the user interface along the x-axis upon a scaling back of at least one of the one or more tolerance-building delivery rates in response to a failure to achieve a desired tolerance during the therapy session, and wherein
 the user interface is further configured to provide a notification in advance of a transition from a first tolerance-building delivery rate to a second tolerance-building delivery rate, the notification is configured to prompt the monitoring of a vital sign and/or condition of the patient prior to the transition, a status of the monitored vital sign and/or condition of the patient prompts the control module to issue a hold dosage flag, and the hold dosage flag is cleared upon the request for an increase in the tolerance-building delivery rate.

2. An ambulatory infusion pump configured to graphically illustrate progress along a programmed step delivery profile during a therapy session, the ambulatory infusion pump comprising:

a pump control system configured to control operation of a pumping mechanism according to one or more delivery rates defined by the programmed step delivery profile; and a control module in communication with the pump control system, the control module including a user interface presenting an indicator graphic along with a step delivery profile graphic configured to illustrate progress along the step delivery profile during the therapy session, wherein the user interface is further configured to provide a notification in advance of a transition from a first tolerance-building delivery rate to a second tolerance-building delivery rate, the notification configured to prompt the monitoring of a vital sign and/or condition of the patient prior to the transition, wherein a status of the monitored vital sign and/or condition of the patient prompts the control module to issue a hold dosage flag, and wherein the hold dosage flag is cleared upon the request for an increase in the tolerance-building delivery rate.

3. The ambulatory infusion pump of claim 2, wherein the pumping mechanism is configured to dispense medicament for a treatment of at least one of an immune deficiency, inflammation disorder, autoimmune disorder, and/or acute infection.

4. The ambulatory infusion pump of claim 3, wherein the medicament is an intravenous immunoglobulin (IVIG).

5. The ambulatory infusion pump of claim 2, wherein the control module enables adjustment of the step delivery profile during the therapy session in response to a failure of a patient to achieve a desired tolerance at any given delivery rate.

6. An ambulatory infusion pump configured to deliver medicament according to a customized delivery profile that enables a patient to gradually build up a tolerance to the medicament during a therapy session, the ambulatory infusion pump comprising:

a pump control system configured to control operation of a pumping mechanism according to one or more tolerance-building delivery rates defined by a step delivery profile; and a control module in communication with the pump control system, the control module including a user interface presenting an indicator graphic along with a step delivery profile graphic configured to illustrate progress along the step delivery profile during the therapy session, wherein the user interface is further configured to provide a notification in advance of a transition from a first tolerance-building delivery rate to a second tolerance-building delivery rate, the notification configured to prompt the monitoring of a vital sign and/or condition of the patient prior to the transition, wherein a status of the monitored vital sign and/or condition of the patient prompts the control module to issue a hold dosage flag, and wherein the hold dosage flag is cleared upon the request for an increase in the tolerance-building delivery rate.

* * * * *